United States Patent
Thorlaksen et al.

(10) Patent No.: US 9,920,216 B2
(45) Date of Patent: Mar. 20, 2018

(54) CURING AGENT FOR TIE-COAT COMPOSITION COMPRISING AN AMINO-SILANE ADDUCT

(71) Applicant: HEMPEL A/S, Kgs. Lyngby (DK)

(72) Inventors: Peter Christian Weinrich Thorlaksen, Solrød Strand (DK); Andreas Lundtang Paulsen, Vanløse (DK)

(73) Assignee: HEMPEL A/S, Lyngby (DK)

( * ) Notice: Subject to any disclaimer, the term of this patent is extended or adjusted under 35 U.S.C. 154(b) by 370 days.

(21) Appl. No.: 14/772,498

(22) PCT Filed: Mar. 21, 2014

(86) PCT No.: PCT/DK2014/050069
§ 371 (c)(1),
(2) Date: Sep. 3, 2015

(87) PCT Pub. No.: WO2014/166492
PCT Pub. Date: Oct. 16, 2014

(65) Prior Publication Data
US 2016/0017172 A1 Jan. 21, 2016

(30) Foreign Application Priority Data
Mar. 27, 2013 (EP) .................................... 13161381

(51) Int. Cl.
| | | |
|---|---|---|
| C09D 163/00 | (2006.01) | |
| C07F 7/08 | (2006.01) | |
| C07F 7/18 | (2006.01) | |
| C09D 5/16 | (2006.01) | |
| B05D 1/02 | (2006.01) | |
| B05D 1/42 | (2006.01) | |
| B05D 3/04 | (2006.01) | |
| B32B 7/12 | (2006.01) | |
| B32B 37/12 | (2006.01) | |

(52) U.S. Cl.
CPC .............. *C09D 163/00* (2013.01); *B05D 1/02* (2013.01); *B05D 1/42* (2013.01); *B05D 3/0406* (2013.01); *C07F 7/081* (2013.01); *C07F 7/18* (2013.01); *C09D 5/1693* (2013.01); *B32B 7/12* (2013.01); *B32B 2037/1269* (2013.01); *B32B 2307/754* (2013.01)

(58) Field of Classification Search
CPC ....... C08L 63/00; C08L 83/06; C09D 163/00; C09D 183/06
See application file for complete search history.

(56) References Cited

U.S. PATENT DOCUMENTS

| | | | |
|---|---|---|---|
| 6,110,536 A | 8/2000 | Harblin | |
| 6,391,464 B1 | 5/2002 | Harblin | |
| 2007/0092738 A1* | 4/2007 | Gronlund Scholten | |
| | | | ............................ C09D 5/002 |
| | | | 428/448 |
| 2015/0353741 A1* | 12/2015 | Liao ..................... C09D 5/1637 |
| | | | 428/413 |
| 2015/0368506 A1* | 12/2015 | Niimoto .................. B32B 15/08 |
| | | | 428/418 |

FOREIGN PATENT DOCUMENTS

| | | |
|---|---|---|
| EP | 1 013 437 A1 | 6/2000 |
| EP | 1 013 727 A1 | 6/2000 |
| EP | 1 670 866 | 6/2013 |
| FR | 2 930 778 A1 | 11/2009 |
| WO | WO 96/16109 A1 | 5/1996 |
| WO | WO 00/77102 A1 | 12/2000 |
| WO | WO 01/02506 A1 | 1/2001 |
| WO | WO 01/94446 A1 | 12/2001 |
| WO | WO 02/074870 A1 | 9/2002 |
| WO | WO 2005/033219 A2 | 4/2005 |
| WO | WO 2008/125610 A1 | 10/2008 |
| WO | WO 2010/018164 A1 | 2/2010 |
| WO | WO 2010/149869 A1 | 12/2010 |
| WO | WO 2011/092278 A1 | 8/2011 |
| WO | WO 2013/000479 A1 | 1/2013 |

OTHER PUBLICATIONS

Ash et al. "Handbook of Paint and Coating Raw Materials" Gower Publ. Ltd., Great Britain vol. 1, pp. 821-823 and 849-851, 1996.
Weigel et al. "Epoxidharzlacke" Wissenschaftliche Verlagsgesellschaft M.B.H, Stuttgart, pp. 203-210, 1965.

* cited by examiner

*Primary Examiner* — Marc Zimmer
(74) *Attorney, Agent, or Firm* — Birch, Stewart, Kolasch & Birch, LLP

(57) ABSTRACT

The application discloses a method for applying a fouling-release coating system to a surface, said surface suitably provided with an anticorrosive coat, and an article comprising a substrate, said substrate having a surface, preferably an anticorrosive coat on at least a part of the surface of said substrate and a tie-coat on said substrate. A curing agent composition comprising an amino-silane adduct comprising a high molecular weight amine, HMWA, as well as a tie-coat comprising said curing agent composition are also provided.

20 Claims, No Drawings

CURING AGENT FOR TIE-COAT COMPOSITION COMPRISING AN AMINO-SILANE ADDUCT

FIELD OF THE INVENTION

The present invention relates to a method for applying a fouling-release coating system to a surface. It also provides an article comprising a substrate, said substrate having a surface, and a tie-coat on said surface. A curing agent composition comprising an amino-silane curing agent, and a tie-coat comprising said curing agent composition are also provided.

BACKGROUND OF THE INVENTION

Aquatic structures, in particular immersed marine structures that come in contact with water, especially sea water, have a tendency to become fouled by marine organisms. Antifouling and fouling-release paint systems are abundantly used for such structures, e.g. ships, buoys, watercraft structures, etc. in order to suppress settlement of such marine organisms, or to encourage their release.

Fouling-release coating systems for steel structures typically include three principal layers, namely an epoxy-based anticorrosive layer applied to the steel substrate, a fouling-release layer, and an intermediate layer, often referred to as a "tie-coat", for establishing strong bonding between the otherwise incompatible epoxy-based anticorrosive layer and the polysiloxane-based fouling-release layer.

WO2005/033219 discloses a coating composition comprising at least two types of functional polysiloxane compounds selected from epoxy-functional polysiloxanes, amino-functional polysiloxanes, and particular adhesion promoting agents of the polysiloxane type.

EP 1 013 727 A1, U.S. Pat. Nos. 6,391,464 and 6,110,536 (General Electric Co.) disclose an epoxy-silicone adhesive paint as a tie-coat for a fouling-release coating. The paint comprises 80-85% by weight of an epoxy resin paint, and 15-20% by weight of a silicon-based adhesion promoter. The silicon adhesive promoter comprises a volatile hydrocarbon solvent, a partially condensed organosilicate, a solubilized metallic catalyst, and an aminoalkyltrialkoxysilane.

EP1670866 discloses a fouling release tie-coat composition.

Typically, tie-coat compositions have proven difficult to provide good adhesion at low temperatures at the interface between the primer or anticorrosive composition (typically an epoxy, acrylic or polyurethane coating) to the mainly polysiloxane based composition (typically a silicone based tie-coat or a silicone based topcoat). Blistering is also a problem and is often the cause of adhesion loss.

In view of the above, there is a need for improved or at least alternative tie-coat compositions for fouling-release coating. In particular, there is a need for tie-coat systems which are able to provide strong bonding between a surface and a polysiloxane based layer even at low application temperatures of the compositions.

SUMMARY OF THE INVENTION

It has been found by the present inventor(s) that, tie-coat compositions comprising a particular class of curing agents provide effective adhesion between a surface (e.g. an anticorrosive layer) and a fouling-release layer, even at low application temperatures.

Curing of a tie-coat composition according to the invention involves three main processes: evaporation of solvent, epoxy-amine addition and siloxane condensation. Effective curing is not simply a question of speeding up these processes individually, but is instead a question of obtaining the correct balance between them, so that the entire curing process is enabled at low temperature, such as applications below 15°, e.g. below 10° C., such as below 5° C. So, in a first aspect the present invention relates to a method for applying a fouling-release coating system to a surface, suitably anticorrosive coat, said method comprising the steps of: (a) applying a tie-coat composition to the surface and (b) subsequently applying a fouling-release top-coat. The tie-coat composition comprises:

i) a binder system comprising an epoxy resin;
ii) one or more adhesion-promoting agents selected from the group consisting of hydroxy-functional polysiloxanes and $C_{1-4}$-alkoxy-functional polysiloxanes; and
iii) an amino-silane adduct of the formula I:

$$\text{HMWA-}\{N(Y)\text{-}Q\text{-}X\text{—}Z\}_p \quad (I)$$

wherein HMWA-N(Y)—, p, Q, $R^1$, $R^2$, $R^3$, $R^4$, X and Z are as defined herein, and wherein the weight average molecular weight of the amino-silane adduct of the formula I is in the range of 500-20000 g/mol.

An aspect is also envisaged in which the adhesion-promoting agent(s) are optional, (b) a condensation-curing tie-coat is applied to the tie-coat of step (a); followed by (c) subsequently applying a fouling-release top-coat.

The invention also provides an article comprising a substrate, said substrate having a surface, and a tie-coat on said surface, wherein the tie-coat is prepared from a tie-coat composition comprising constituents i., ii. and iii. as defined herein. An article comprising a substrate, said substrate having a surface and a first tie-coat on said surface is also provided, wherein the first tie-coat is prepared from a tie-coat composition in which constituent ii. is optional, said article additionally comprising a condensation-curing tie-coat on said first tie-coat.

The invention provides a curing agent composition comprising an amino-silane adduct of the formula (Ia) or formula (Ib):

(Ia)

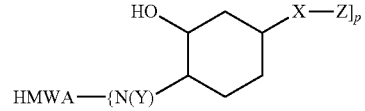

(Ib)

where HMWA-N(Y)—, $R^1$, $R^2$, p, X and Z are as defined herein and wherein the weight average molecular weight of the amino-silane adduct of the formula Ia is in the range of 500-20000 g/mol.

A tie-coat composition comprising the curing agent composition according to the invention is also provided.

Further details of the invention are set out in the dependent claims and the following description.

DETAILED DISCLOSURE OF THE INVENTION

In a first aspect, the present invention therefore provides a method for applying a fouling-release coating system to a surface, in which the surface is suitably an anticorrosive coat.

The term "substrate" is intended to mean a solid material onto which a coating composition may be applied. The substrate typically comprises a metal such as steel, iron, aluminium, or a glass-fibre. In the most interesting embodiments, the substrate is a metal substrate, in particular a steel substrate. In an alternative embodiment, the substrate is a glass-fibre substrate.

The term "surface" is used in its normal sense, and refers to the exterior boundary of an object upon which the fouling-release coating system of the invention is applied. As such, the surface of the substrate may either be the "native" surface (e.g. the steel surface). However, the substrate is typically coated, e.g. with an anticorrosive coating, so that the surface of the substrate is constituted by such a coating. Alternatively, the substrate may carry a paint coat, e.g. a worn-out antifouling coat or similar. When present, the anticorrosive coat is typically applied in a total dry film thickness of 100-600 µm, such as 150-450 µm, e.g. 200-400 µm.

Particular examples of surfaces suitable for coating according to the invention are surfaces of vessels (including but not limited to boats, yachts, motorboats, motor launches, ocean liners, tugboats, tankers, container ships and other cargo ships, submarines, and naval vessels of all types), pipes, shore and off-shore machinery, constructions and objects of all types such as piers, pilings, bridge substructures, water-power installations and structures, underwater oil well structures, nets and other aquatic culture installations, and buoys, etc.

The anticorrosive coat is typically an epoxy-based coat. Suitable epoxy-based coats are described in co-pending patent applications WO 08/125610 and WO 11/092278.

The term "epoxy-based coat" should be construed as the combination of the one or more epoxy resins, one or more curing agents, any reactive epoxy diluents and any reactive acrylic modifiers.

The "epoxy-based coat" comprises one or more epoxy resins selected from aromatic or non-aromatic epoxy resins (e.g. hydrogenated epoxy resins), containing more than one epoxy group per molecule, which is placed internally, terminally, or on a cyclic structure, together with one or more suitable curing agents to act as cross-linking agents. Combinations with reactive diluents from the classes mono functional glycidyl ethers or esters of aliphatic, cycloaliphatic or aromatic compounds can be included in order to reduce viscosity and for improved application and physical properties.

Suitable epoxy-based coats are believed to include epoxy and modified epoxy resins selected from bisphenol A, bisphenol F, Novolac epoxies, non-aromatic epoxies, cycloaliphatic epoxies, epoxidised polysulfides, glycidyl esters and epoxy functional acrylics or any combinations hereof.

The epoxy-based coat also comprises one or more curing agents selected from compounds or polymers comprising at least two reactive hydrogen atoms linked to nitrogen.

Suitable curing agents are believed to include amines or amino functional polymers selected from aliphatic amines and polyamines (e.g. cycloaliphatic amines and polyamines), polyamidoamines, polyoxyalkylene amines (e.g. polyoxyalkylene diamines), aminated polyalkoxyethers (e.g. those sold commercially as "Jeffamines"), alkylene amines (e.g. alkylene diamines), aralkylamines, aromatic amines, Mannich bases (e.g. those sold commercially as "phenalkamines"), amino functional silanes, and including epoxy adducts and derivatives thereof. The skilled person would know, that epoxy adducts are reaction products of a substoichiometric amount of an epoxy with one or more amines comprising an active hydrogens bonded to nitrogen atoms as described in Kurt Weigel "EPDXIDHARZLACKE", 1965, Wissenschaftliche Verlagsgesellschaft M.B.H, Stuttgart, pp 203-210.

The term "applying" is used in its normal meaning within the paint industry. Thus, "applying" is conducted by means of any conventional means, e.g. by brush, by roller, by spraying, by dipping, etc. The commercially most interesting way of "applying" the coating composition is by spraying. Spraying is effected by means of conventional spraying equipment known to the person skilled in the art. The coating is typically applied in a dry film thickness of 20-900 µm, such as 20-750 µm, e.g. 50-600 µm. According to a first aspect of the invention, the method comprises the steps of (a) applying a tie-coat composition to the surface, and (b) subsequently applying a fouling-release top-coat.

According to a second aspect of the invention, the method comprises the steps of (a) applying a tie-coat composition to the surface, (b) applying a condensation-curing tie-coat to the tie-coat of step (a); and (c) subsequently applying a fouling-release top-coat.

In embodiments of either aspect, the tie-coat composition is applied to an anticorrosive coat upon said surface; alternatively, the tie-coat composition can be applied to a fouling-release coat upon said surface; alternatively, the tie-coat composition can be applied to an antifouling coat. Typically, in an embodiment thereof, the tie-coat composition is applied to an anticorrosive coat upon said surface; alternatively, the tie-coat composition can be applied to a fouling-release coat upon said surface. In another embodiment thereof, the tie-coat composition is applied to an anticorrosive coat upon said surface; alternatively, the tie-coat composition can be applied to an antifouling coat. In a specific embodiment thereof, tie-coat composition is applied to an anticorrosive coat upon said surface. In another specific embodiment thereof, the tie-coat composition is applied to an antifouling coat upon said surface.

In embodiments of either aspect, the tie-coat composition is applied to an epoxy-based coat, such as a primer. In an embodiment said tie-coat has dual function and also possess anticorrosive properties. In an embodiment thereof, the tie-coat of the present invention replaces an anticorrosive coat thus reducing the total number of layers in the coating system with one anticorrosive layer. Coating systems conventionally used in the art generally include 2 anticorrosive coats, in those cases, dual function tie-coat compositions of the present invention will reduce the number of anticorrosive coats to 1.

In some embodiments, the tie-coat of the present invention is applied on an old epoxy based coat which has been:
washed to remove contaminants, or
washed to remove contaminants and roughened by means of sanding, sweeping or the like.

According to further embodiments of the invention, the method comprises the steps of applying more than one layer of fouling release topcoat(s) on either of the aspects disclosed herein.

In the first aspect of the invention, the tie-coat composition comprises three main constituents:
  i) a binder system comprising an epoxy resin;
  ii) one or more adhesion-promoting agents selected from the group consisting of hydroxy-functional polysiloxanes and $C_{1-4}$-alkoxy-functional polysiloxanes; and
  iii) an amino-silane adduct of the formula I:

$$HMWA\text{-}\{N(Y)\text{-}Q\text{-}X\text{—}Z\}_p \quad (I)$$

In the second aspect of the invention (in the case where a condensation-curing tie-coat is present between the tie-coat of the invention and a fouling-release top-coat) the tie-coat composition comprises two main constituents, plus an optional constituent; i.e.
i) a binder system comprising an epoxy resin;
ii) optionally, one or more adhesion-promoting agents selected from the group consisting of hydroxy-functional polysiloxanes and $C_{1-4}$-alkoxy-functional polysiloxanes; and
iii) an amino-silane adduct of the formula I:

HMWA-{N(Y)-Q-X—Z}$_p$     (I)

In an embodiment of this second aspect, the tie-coat composition comprises:
i) a binder system comprising an epoxy resin;
ii) one or more adhesion-promoting agents selected from the group consisting of hydroxy-functional polysiloxanes and $C_{1-4}$-alkoxy-functional polysiloxanes; and iii) an amino-silane adduct of the formula I:

HMWA-{N(Y)-Q-X—Z}$_p$     (I)

In another embodiment of this second aspect, the tie-coat composition comprises:
i) a binder system comprising an epoxy resin; and
ii) an amino-silane adduct of the formula I:

HMWA-{N(Y)-Q-X—Z}$_p$     (I)

The various constituents will be described in more detail in the following:

Epoxy-Based Binder System

The first constituent of the tie-coat composition according to both aspects of the invention is an epoxy-based binder system (=a binder system comprising an epoxy resin). The term "epoxy-based binder system" should be construed as the combination of one or more epoxy resins, any curing agents, any reactive epoxy diluents, any epoxy modifiers, and any extender resins.

The epoxy-based binder system may comprise one or more epoxy resins selected from aromatic or non-aromatic epoxy resins (e.g. hydrogenated epoxy resins), containing more than one epoxy group per molecule, which is placed internally, terminally, or on a cyclic structure, together with any suitable curing agent to act as cross-linking agent. In an embodiment of the present invention, said epoxy resin is selected from the group of aromatic epoxy resins. In a further embodiment, said epoxy resin is selected from the group of epoxy resins having 2 epoxy groups on each molecule. In a specific embodiment hereof, the epoxy resin is based on bisphenol A and/or bisphenol F. In another a specific embodiment hereof, the epoxy resin is based on a molecule consisting of 2 or more bisphenol A or bisphenol F units or mixtures thereof. In a further embodiment, said epoxy resin is selected from the group of epoxy resins having more than 2 epoxy groups on each molecule. In variant specific embodiment hereof, the epoxy resin is a novolac based on bisphenol A or bisphenol F. In another specific embodiment thereof, the epoxy resin is based on bisphenol A and contains a pendant hydroxyl group.

Combinations with reactive diluents such as from the classes mono functional glycidyl ethers or esters of aliphatic, cycloaliphatic or aromatic compounds can be included in order to reduce viscosity and for improved application and physical properties.

Suitable epoxy-based binder systems are believed to include epoxy and modified epoxy resins selected from bisphenol A, bisphenol F, Novolac epoxies, non-aromatic epoxies, cycloaliphatic epoxies, rubber modified epoxies, epoxidised polysulfides, glycidyl esters and epoxy functional acrylics or any combinations hereof. A particular epoxy-based binder system includes bisphenol A. In an embodiment thereof, the epoxy resin included in the epoxy-based binder system is selected from the group consisting of bisphenol A, bisphenol F and Novolac epoxies. In a further embodiment, said epoxy resin contains a mixture of bisphenol A, bisphenol F, Novolac epoxies. In yet a further embodiment, said epoxy resin is made of bisphenol A. In yet a further embodiment, said epoxy resin is made of bisphenol F. In yet a further embodiment, said epoxy resin is made of Novolac epoxies.

Examples of suitable commercially available solvent-borne epoxy resins are:
Epikote 828, ex. Momentive (US), bisphenol A type
Araldite GY 250, ex. Huntsman Advanced Materials (Switzerland), bisphenol A type
Epikote 1004, ex. Momentive (US) bisphenol A type
DER 664-20, ex. Dow Chemicals (Germany), bisphenol A type
Epikote 1001X75, ex. Momentive (US), bisphenol A type
Araldite GZ 7071X75BD, ex. Huntsman Advanced Materials (Germany), bisphenol A type in xylene
Araldite GZ 7071X75CH, ex. Huntsman Advanced Materials (Switzerland), bisphenol A type
DER 352, ex. Dow Chemicals (Germany), mixture of bisphenol A and bisphenol F
Epikote 235, ex. Momentive (US), mixture of bisphenol A and bisphenol F
Epikote 862, ex. Momentive (US), bisphenol F type
DEN 438-X 80, ex. Dow Chemical Company (USA), epoxy novolac
Epikote 1009, ex. Momentive (US), bisphenol A type
DER 684-EK40, ex. Dow Chemicals (Germany), bisphenol A type
Epikote 154, ex. Momentive (US) epoxy novolac Further to the curing agent of formula (I) disclosed herein, the tie coat composition may further comprise a curing agent which is not an amino-silane adduct. Accordingly, the epoxy-based binder system may comprise one or more curing agents conventionally used in the art. Accordingly, the epoxy-based binder system may comprise one or more curing agents selected from compounds or polymers comprising at least two reactive hydrogen atoms linked to nitrogen.

Suitable curing agents for solvent-borne epoxy resins are believed to include amines or amino functional polymers selected from aliphatic amines and polyamines (e.g. cycloaliphatic amines and polyamines), polyamidoamines, polyoxyalkylene amines (e.g. polyoxyalkylene diamines), aminated polyalkoxyethers (e.g. those sold commercially as "Jeffamines"), alkylene amines (e.g. alkylene diamines), aralkylamines, aromatic amines, Mannich bases (e.g. those sold commercially as "phenalkamines"), isocyanates, and including amine adducts and derivatives thereof. In one embodiment, the curing agents are polyamidoamine adducts.

Examples of suitable commercially available curing agents are:
Jeffamine EDR-148 ex. Huntsman Corporation (USA), triethyleneglycoldiamine
Jeffamine D-230 ex. Huntsman Corporation (USA), polyoxypropylene diamine
Jeffamine D-400 ex. Huntsman Corporation (USA), polyoxypropylene diamine Jeffamine T-403 ex. Huntsman Corporation (USA), polyoxypropylene triamine Ancamine 1693 ex. Air Products (USA), cycloaliphatic polyamine adduct Ancamine X2280 ex. Air Products (USA), cycloaliphatic amine Ancamine 2074 ex. Air Products (USA), cycloaliphatic polyamine adduct Ancamide 350 A ex. Air Products (USA), polyaminoamide Sunmide CX-105X, ex. Air Products Inc., Mannich base Epikure 3140 Curing Agent, ex. Momentive (USA), polyamidoamine SIQ Amin 2030, ex. SIQ Kunstharze GmbH (Germany), polyamidoamine Epikure 3115X-70 Curing Agent, ex. Momentive (USA), polyamidoamine SIQ Amin 2015, ex. SIQ Kunstharze GmbH (Germany), polyamidoamine Polypox VH 40309/12, ex. Dow Chemicals (USA), polyoxyalkylene amine CeTePox 1490 H, ex. CTP Chemicals and Technologies for Polymers (Germany), polyoxyalkylene amine Epoxy hardener MXDA, ex. Mitsubishi Gas Chemical Company Inc (USA), aralkyl amine Diethylaminopropylamine, ex. BASF (Germany), aliphatic amine Gaskamine 240, ex. Mitsubishi Gas Chemical Company Inc (USA), aralkyl amine Cardolite Lite 2002, ex. Cardolite Corporation (United States), Mannich base Cardolite (NX5454), ex Cardolite Corporation (United States), Mannich base Aradur 42 BD, ex. Huntsman Advanced Materials (Germany), cycloaliphatic amine Isophorondiamin, ex. BASF (Germany), cycloaliphatic amine Epikure 3090 Curing Agent, ex. Momentive (USA), polyamidoamine adduct with epoxy Crayamid E260 E90, ex. Arkema (France), polyamidoamine adduct with epoxy Crayamid 140, ex. Arkema (France), amino polyamide resin Aradur 943 CH, ex. Huntsman Advanced Materials (Switzerland), alkylene amine adduct with epoxy Aradur 863 XW 80 CH, ex. Huntsman Advanced Materials (Switzerland), aromatic amine adduct with epoxy Cardolite NC-541, ex. Cardolite Corporation (United States), Mannich base Cardolite Lite 2001, ex. Cardolite Corporation (United States), Mannich base Examples of suitable reactive epoxy diluents comprise e.g. mono functional glycidyl ethers or esters of aliphatic, cycloaliphatic or aromatic compounds, e.g.

Araldite DY-E/BD, ex. Huntsman Advanced Materials—Germany

Araldite DY-H/BD, ex. Huntsman Advanced Materials—Germany.

Cardura EIOP, ex Momentive—Netherlands

Araldite DY-D/CH, ex. Huntsman Advanced Materials—Germany.

Epodil 757, ex Air Products, US

PEG-400-DEG, ex Raschig Chemical Division—Germany

Examples of suitable epoxy modifiers comprise e.g. oils, oil derivatives, modified oils such as linseed oil and derivatives thereof, castor oil and derivatives thereof, soy bean oil and derivatives thereof. The skilled person would know, that other suitable epoxy modifiers include plasticizers, examples of which include phthalates, di- and tri-aryl compounds, sulphonamides and polyethers [WO2005033219A2, pp. 27-28]. Examples of suitable extender resins comprise e.g. saturated polyester resins, polyvinylacetate, polyvinylbutyrate, copolymers of vinyl acetate and vinyl isobutyl ether, copolymers of vinyl chloride and vinyl isobutyl ether, of polyvinyl methyl ether, polyvinyl isobutyl ether, polyvinyl ethyl ether, modified aromatic hydrocarbon resins; styrene copolymers such as styrene/butadiene copolymers; acrylic resins; hydroxy-acrylate copolymers; fatty acids; cyclized rubbers and epoxy esters.

In one embodiment, epoxy-based binder systems comprise a) one or more epoxy resins selected from bisphenol A, bisphenol F and Novolac; and b) one or more curing agents selected from Mannich bases, polyamidoamines, polyoxyalkylene amines, alkylene amines, aralkylamines, polyamines, and adducts and derivatives thereof.

In another embodiment, the epoxy resin may have an epoxy equivalent weight of 100-9000, 100-2000, such as 100-1500 e.g. 150-1000, such as 150-700. In a further embodiment, the epoxy resin has an epoxy equivalent weight of 300-600. In a further embodiment, the epoxy resin has an epoxy equivalent weight of 100-350, such as 150-300.

In yet another embodiment, epoxy-based binder systems may comprise one or more bisphenol A epoxy resins having an epoxy equivalent weight of 150-700 and one or more polyamidoamine or adducts and derivatives thereof.

In embodiments of either aspect, the epoxy-based binder system comprises:
  a) one or more epoxy resins selected from bisphenol A, bisphenol F and Novolac; and
  b) one or more curing agents selected from Mannich bases, polyamidoamines, polyoxyalkylene amines, alkylene amines, aralkylamines, polyamines, and adducts and derivatives thereof; and
  c) one or more extender resins selected from saturated polyester resins, polyvinylacetate, polyvinylbutyrate, copolymers of vinyl acetate and vinyl isobutyl ether, copolymers of vinyl chloride and vinyl isobutyl ether, of polyvinyl methyl ether, polyvinyl isobutyl ether, polyvinyl ethyl ether, modified aromatic hydrocarbon resins; styrene copolymers such as styrene/butadiene copolymers; acrylic resins; hydroxy-acrylate copolymers; fatty acids; cyclized rubbers and epoxy esters.

In further embodiments of either aspect, the epoxy-based binder system comprises:
  a) one or more epoxy resins selected from bisphenol A, bisphenol F and Novolac; and
  b) one or more curing agents selected from Mannich bases, polyamidoamines, polyoxyalkylene amines, alkylene amines, aralkylamines, polyamines, and adducts and derivatives thereof; and
  c) one or more extender resins selected from vinyl isobutyl ether, copolymers of vinyl chloride and vinyl isobutyl ether; styrene copolymers such as styrene/butadiene copolymers; acrylic resins; hydroxy-acrylate copolymers; fatty acids; cyclized rubbers and epoxy esters.

In yet another embodiments of either aspect, the epoxy-based binder system comprises:
  a) one or more epoxy resins selected from bisphenol A, bisphenol F and Novolac; and
  b) one or more curing agents selected from Mannich bases, polyamidoamines, polyoxyalkylene amines, alkylene amines, aralkylamines, polyamines, and adducts and derivatives thereof; and c) one or more extender resins selected from vinyl isobutyl ether, copolymers of vinyl chloride and vinyl isobutyl ether.

In yet another embodiments of either aspect, epoxy-based binder systems may comprises:

a) one or more bisphenol A epoxy or bisphenol F epoxy resins having an epoxy equivalent weight of 150-300;

b) and one or more Mannich bases or adducts and derivatives thereof;

c) one or more extender resins selected from vinyl isobutyl ether, copolymers of vinyl chloride and vinyl isobutyl ether.

In yet another embodiments of either aspect, the epoxy-based binder system comprises:

a) one or more epoxy resins selected from bisphenol A, bisphenol F and Novolac; and b) one or more extender resins selected from vinyl isobutyl ether, copolymers of vinyl chloride and vinyl isobutyl ether; styrene copolymers such as styrene/butadiene copolymers; acrylic resins; hydroxy-acrylate copolymers; fatty acids; cyclized rubbers and epoxy esters.

In yet another embodiments of either aspect, the epoxy-based binder system comprises a) one or more epoxy resins selected from bisphenol A, bisphenol F and Novolac; and b) one or more extender resins selected from acrylic resins, vinyl isobutyl ether, copolymers of vinyl chloride and vinyl isobutyl ether.

In yet another embodiments of either aspect, epoxy-based binder systems may comprise one or more bisphenol A epoxy or bisphenol F epoxy resins having an epoxy equivalent weight of 150-300 and one or more extender resins selected from acrylic resins, vinyl isobutyl ether, copolymers of vinyl chloride and vinyl isobutyl ether.

In one embodiment, the epoxy-based binder systems may comprise one or more plasticizer such as phthalates, di- and tri-aryl compounds, sulphonamides and polyethers.

In one embodiment, epoxy-based binder systems are ambient curing binder systems.

In the tie-coat composition, the total amount of epoxy-based binder system (component i.) may be in the range of 10-90%, such as 20-70%, e.g. 30-50%, by solids volume of the tie-coat composition. In a further embodiment, said total amount of epoxy-based binder system (component i.) is in the range of 20-60%, such as 20-40%, by solids volume of the tiecoat composition. In another embodiment, said total amount of epoxy-based binder system (component i.) is in the range of 10-60%, such as 10-40%, e.g. 15-30% by solids volume of the tiecoat composition. In another embodiment, said total amount of epoxy-based binder system (component i.) is in the range of 40-90%, such as 50-80%, e.g. 50-60% by solids volume of the tiecoat composition.

When used herein, the term "hydrogen equivalents" is intended to cover only reactive hydrogen atoms linked to nitrogen.

The number of "hydrogen equivalents" in relation to the one or more curing agents is the sum of the contribution from each of the one or more curing agents. The contribution from each of the one or more curing agents to the hydrogen equivalents is defined as grams of the curing agent divided by the hydrogen equivalent weight of the curing agent, where the hydrogen equivalent weight of the curing agent is determined as: grams of the curing agent equivalent to 1 mol of active hydrogen. For adducts with epoxy resins the contribution of the reactants before adduction is used for the determination of the number of "hydrogen equivalents" in the epoxy-based binder system.

The number of "epoxy equivalents" in relation to the one or more epoxy resins is the sum of the contribution from each of the one or more epoxy resins. The contribution from each of the one or more epoxy resins to the epoxy equivalents is defined as grams of the epoxy resin divided by the epoxy equivalent weight of the epoxy resin, where the epoxy equivalent weight of the epoxy resin is determined as: grams of the epoxy resin equivalent to 1 mol of epoxy groups. For adducts with epoxy resins the contribution of the reactants before adduction is used for the determination of the number of "epoxy equivalents" in the epoxy-based binder system.

The ratio between the hydrogen equivalents of the one or more curing agents and the epoxy equivalents of the one or more epoxy resins may be in the range of 20:100 to 200:100, such as in the range 50:100 to 130:100 or 60:100 to 130:110, or such as 80:100 to 140:100. In a further embodiment, said ratio is in the range of 80:100 to 110:100, such as 85:100 to 105:100 or 80:100 to 95:100.

Adhesion-Promoting Agent

The tie-coat composition according to the first aspect of the invention comprises one or more adhesion promoting agents selected from the group consisting of hydroxy-functional polysiloxanes, and $C_{1-4}$-alkoxy-functional polysiloxanes. In the second aspect of the invention, this component is optional. In one further embodiments of the invention, the tie-coat composition is devoid of adhesion promoting agents selected from the group consisting of hydroxy-functional polysiloxanes, and $C_{1-4}$-alkoxy-functional polysiloxanes. In a further embodiment, the tie-coat composition is devoid of any adhesion promoting agents.

In one embodiment, the adhesion promoting agent (ii) is omitted and an intermediate, condensation curing, organopolysiloxane is introduced between the tie-coat composition according to the invention and the fouling release topcoat. In one variant hereof, the intermediate condensation curing organopolysiloxane composition is a condensation curing RTV-1, such as a composition of the structure, formula [IV]:

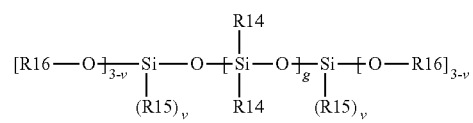

of which R14 is independently selected from $C_{1-8}$-alkyl (such as methyl, ethyl, n-propyl, isopropyl, n-butyl, n-pentyl, n-hexyl, 2-ethyl hexyl and n-octyl), $C_{4-8}$-cycloalkyl (such as cyclopentyl, cyclohexyl and methylcyclohexyl), $C_{2-4}$-alkenyl (such as vinyl, allyl or buten-2-yl), aryl (such as phenyl) and aryl-$C_{1-4}$-alkyl (such as tolyl and xylyl); R15 is independently selected from $-CH_3$, $-C_2H_5$, $-CH=CH_2$ and $-C_6H$; R16 is independently selected from $C_{1-4}$-alkyl, such as methyl, ethyl, n-propyl, isopropyl, n-butyl; $-N=C(C_{1-4}$ alkyl)($C_{1-4}$ alkyl) such as $-N=C(CH_3)(CH_2CH_3)$ or $-N=C(CH_3)_2$; v is an integer between 0 and 2 and g is an integer in the range of 100-10000, such as 100-5000, such as 150-1000.

In another embodiment, the adhesion promoting agent (ii) is a silanol terminated polysiloxane and an intermediate, condensation curing, organopolysiloxane is introduced between the tie-coat composition according to the invention and the fouling release topcoat. In one variant hereof, intermediate condensation curing organopolysiloxane composition is an oxime curing RTV-1, according to formula [IV].

In yet another embodiment, the adhesion promoter is a condensation curing organopolysiloxane, according to formula [VI].

In another embodiment, the adhesion promoter is a silanol terminated organopolysiloxane according to formula [V]

Without being bound to any particular theory, the term "adhesion promoting agent" is intended to mean that the agent in question has a beneficial impact on adhesion between the tie-coat and a subsequent layer applied onto the tie-coat.

In one embodiment, the adhesion promoting agent is a polydiorganosiloxane of viscosity 60-10,000 mPas, such as 60-5,000 mPas, e.g. 60-1000 mPas, at 25° C. Other viscosities include 50-750 mPas, such as 60-300 mPas or 60-150 mPas, even 100-750 mPas such as 500-750 mPas.

In an embodiment, the adhesion promotion agent is selected from the group of silanol terminated polysiloxanes, identified by the general structure below Formula (V):

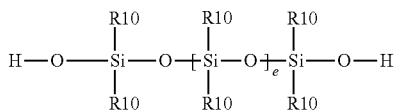

where R10 is independently selected from $C_{1-8}$-alkyl (such as methyl, ethyl, n-propyl, isopropyl, n-butyl, n-pentyl, n-hexyl, 2-ethyl hexyl and n-octyl), $C_{4-8}$-cycloalkyl (such as cyclopentyl, cyclohexyl and methylcyclohexyl), $C_{2-4}$-alkenyl (such as vinyl, allyl or buten-2-yl), aryl (such as phenyl) and aryl-$C_{1-4}$-alkyl (such as tolyl and xylyl) and e is an integer in the range of 4-1000, such as 10-250. In another embodiment, the R10 is a methyl group and the viscosity of the adhesion promoter is in the interval 60-750 mPas, such as 60-300 mPas, even 60-150 mPas.

In another embodiment, the adhesion promoter is a moisture curable polydiorganosiloxane of the structure (VI)

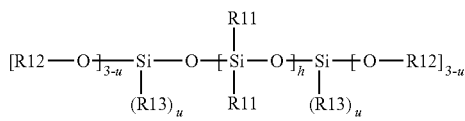

in which R11 is independently selected from $C_{1-8}$-alkyl (such as methyl, ethyl, n-propyl, isopropyl, n-butyl, n-pentyl, n-hexyl, 2-ethyl hexyl and n-octyl), $C_{4-8}$-cycloalkyl (such as cyclopentyl, cyclohexyl and methylcyclohexyl), $C_{2-4}$-alkenyl (such as vinyl, allyl or buten-2-yl), aryl (such as phenyl) and aryl-$C_{1-4}$-alkyl (such as tolyl and xylyl); R13 independently is selected from —$CH_3$, —$C_2H_5$, —CH=$CH_2$ and —$C_6H_5$, R12 is selected from $C_{1-4}$-alkyl, such as methyl, ethyl, n-propyl, isopropyl, n-butyl; —N=C($C_{1-4}$ alkyl)($C_{1-4}$ alkyl) such as —N=C($CH_3$)($CH_2CH_3$) or —N=C($CH_3$)$_2$, u is an integer between 0 and 2 and h is an integer in the range of 4-1000, such as 10-250. In an embodiment of the moisture curable polydiorganosiloxane of the structure (VI), the viscosity is in the interval 60-750 mPas, such as 60-300 mPas, even 100-200 mPas.

The adhesion promoter preferably contains silicon-bonded terminally positioned hydroxyl groups, for example an α,ω-dihydroxy-polydiorganosiloxane, or silicon-bonded hydrolysable groups in a terminal position, for example a moisture curable polydiorganosiloxane tipped with silicon-bonded hydrolysable groups such as $C_{1-4}$-alkoxy groups (e.g. methoxy groups), oximes of the type —O—N=C($C_{1-4}$ alkyl)($C_{1-4}$ alkyl) (e.g. methyl ethyl oxime). More preferably, the adhesion promoting agent is formed of recurring diorganosiloxy units of the formula —Si($R^I$)$_2$O—, wherein $R^I$ is selected from $C_{1-8}$-alkyl (such as methyl, ethyl, n-propyl, isopropyl, n-butyl, n-pentyl, n-hexyl, 2-ethyl hexyl and n-octyl), $C_{4-8}$-cycloalkyl (such as cyclopentyl, cyclohexyl and methylcyclohexyl), $C_{2-4}$-alkenyl (such as vinyl, allyl or buten-2-yl), aryl (such as phenyl) and aryl-$C_{1-4}$-alkyl (such as tolyl and xylyl). In another instance, in addition to the terminal reactivity discussed above, one or more of the organic $R^I$ groups on the recurring unit may comprise a reactive group different from the terminal reactivity, such as an amine containing substituent, e.g. —$NH_2$ or —N(H)—, which may be bonded directly to the silicon atom or, more preferably, via a bridging alkyl group such as —$C_1$-$C_4$ and the substituent may comprise more than one amine, e.g. an aminoethylaminopropyl group.

More specific examples of suitable α,ω-dihydroxypolydiorganosiloxanes are those of the formula HO—[Si($R^{II}$)$_2$O]$_n$—H wherein each $R^{II}$ independently is selected from methyl and phenyl, and where n is an integer in the range of 4-1000, such as 10-250.

More specific examples of suitable moisture curable polysiloxanes are those of the formula (O$R^{III}$)$_{3-m}$Si($R^{IV}$)$_m$O—[Si($R^{IV}$)$_2$O]$_n$—Si—($R^{IV}$)$_m$(O$R^{III}$)$_{3-m}$ wherein each $R^N$ is independently is selected from —$CH_3$, —$C_2H_5$, —CH=$CH_2$ and —$C_6H_5$. $R^{III}$ further includes —N=C($CH_3$)($CH_2CH_3$) or —N=C($CH_3$)$_2$ in addition to the species covered by $R^N$, and where n is an integer in the range of 4-100, such as 10-50, and where m is an integer from 0-2.

Examples of the adhesion promoting agent are particularly those selected from the group consisting of hydroxy-functional polysiloxanes and $C_{1-4}$-alkoxy-functional polysiloxanes, in particular hydroxy-functional polysiloxanes and $C_{1-4}$-alkoxy-functional polysiloxanes, e.g. those illustrated immediately above.

Illustrative examples of commercially available polysiloxane adhesion promoting agents are Rhodorsil oil 48V750 (silanol-functional polydimethylsiloxane) ex Bluestar; Xiameter® PMX-0156 SILANOL FLUID; BY 16-392 (dimethyl, (aminoethylaminopropyl) methylsiloxane, hydroxy-terminated) ex Dow Corning Toryo etc.

Adhesion promoting agents selected from the type α,ω-dihydroxypolydiorganosiloxanes are particularly preferred.

When present, the tie-coat composition comprises 0.1-20%, or 0.1-20%, such as 0.1-15%, e.g. 0.5-10%, by wet weight of the adhesion promoting agent(s).

In some advantageous embodiments, the (weight) average molecular weight, $M_w$ of the adhesion promoting agent is less than 50,000 g/mol, or less than 25,000 g/mol, e.g. 500-50,000 g/mol, or 1000-10,000 g/mol.

Amino-Silane Curing Agent

In both aspects of the invention, the tie-coat composition comprises an amino-silane adduct of the formula (I), above. In formula (I), HMWA-N(Y)— is a High-Molecular Weight Amine moiety comprising three or more amino groups, preferably 4 or more amino groups, at least some of which are primary or secondary amino groups. In one embodiment, the HMWA moiety comprises at least one phenolic moiety. The HMWA moiety may comprise at least one $C_{7-20}$-aliphatic moiety, such as $C_{7-20}$-aliphatic moieties independently selected from alkanes and alkenes. In particular embodiments, said at least one $C_{7-20}$-aliphatic moiety is selected from the group of alkanes and alkenes, wherein said alkenes may comprise up to 5 double bonds, e.g. up to 4 double bonds, preferably 1, 2 or 3 double bonds. In specific embodiments, said at least one $C_{12-17}$-aliphatic moiety is independently selected from the group consisting of —$(CH_2)_7CH$=$CH(CH_2)_5CH_3$, —$(CH_2)_7CH$=$CHCH_2CH$=$CH(CH_2)_2CH_3$, and —$(CH_2)_7CH$=$CHCH_2CH$=$CHCH_2CH$=$CH_2$. Preferably, the HMWA moiety is the Mannich condensation reaction product of a $C_{7-20}$-alkyl phenol (in particular cardanol), formaldehyde and one or more amine(s) selected from diamines, triamines or tetraamines, and optionally further reacted with a substoichiometric amount of an epoxy-functional resin.

Preferred polyamines for use in forming HMWA are: ethylene diamine (EDA); m-phenylenebis(methylamine) (MXDA); diethylenetriamine (DETA); triethylenetriamine (TETA); tetraethylenepentamine (TEPA); 1,3-cyclohexanedimethanamine (1,3-BAC); isophorone diamine (IPD); 1,6-hexanediamine; 2,2,4-trimethyl-(TMD). Other suitable polyamines are to be found in patent publication CA 1082229 A. In a further embodiment, polyamines for use in forming HMWA are e.g. ethylene diamine (EDA); diethylenetriamine (DETA); triethylenetriamine (TETA); tetraethylenepentamine (TEPA) or); 1,6-hexanediamine; 2,2,4-trimethyl-(TMD). In a specific embodiment, the preferred polyamines for use in forming HMWA are selected from the group consisting of ethylene diamine (EDA) and m-phenylenebis(methylamine) (MXDA); such as ethylene diamine (EDA); or such as m-phenylenebis(methylamine) (MXDA).

In one preferred embodiment, the HMWA has been further reacted with a substoichiometric amount of epoxy-functional resin of the type described in the section "epoxy based binder system" to form an adduct. In this embodiment, suitable epoxy functional resins include e.g. Bisphenol A based epoxy resins, Bisphenol F based epoxy resins and the novolac type epoxy resins.

In the curing agent of formula (I), each —N(Y)— is a secondary or tertiary amine, wherein Y is selected from hydrogen and $C_{1-4}$-alkyl. Suitably, Y is hydrogen.

p is 1-20, preferably 1-15, more preferably 2-10.

-Q- is selected from —$C(R^1)_2$—$C(R^2)(OH)$—, —$C(=O)$—$N(R^3)$—, —$C(R^1)_2$—$C(R^1)_2$—$C(=O)$—$O$—, —$C(R^1)_2$—$C(R^1)_2$—$C(=O)$—$N(R^4)$— and

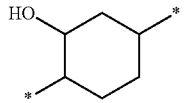

in which each $R^1$ and $R^2$ are independently selected from hydrogen and $C_{1-4}$-alkyl; and $R^3$ and $R^4$ are independently selected from hydrogen, $C_{1-8}$-linear or branched alkyl, vinyl, allyl, aryl and aryl-$C_{1-4}$-alkyl. Preferably, Q is —$C(R^1)_2$—$C(R^2)(OH)$—. Suitably, $R^1$ and $R^2$ are both hydrogen. The skilled person would understand that * is defined by being a bridging, covalent bond.

In a preferred embodiment, Q is defined by being of the structure —[$CH_2$—$CH(OH)$]—

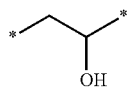

In another embodiment, Q is defined by being of the structure:

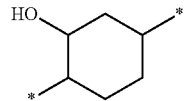 [SMILES: *C1CCC(*)C(O)C1]

—X— is a linker moiety selected from $C_{1-6}$-alkylene which may be optionally substituted with one or more substituents selected from hydroxyl and $C_1$-$C_4$ alkyl; —(CO)—; —NR*—; —O—; —NR*—C(=O)—NR*—; —NR*—C(=O)—; —C(=O)—NR*; -arylene; and combinations thereof, in which R* is selected from H and $C_{1-6}$-alkyl. In some embodiments, X is selected from the group consisting of hydroxyl and $C_1$-$C_4$ alkyl; —(CO)—; —O—; and combinations thereof. In a specific embodiment, X is selected from the group consisting of $C_1$-$C_4$ alkyl and —O—; and combinations thereof. Suitably, X is $C_{1-6}$-alkylene. Included in this definition are linker moieties X in which X is a poly(alkylether), polyamine, polyamide or polyurea linker moiety.

In one preferred embodiment, X is is an alkylether, such as an alkylether defined by the structure

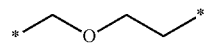

In another embodiment, X is a methylene bridge, —[$CH_2$]—.

—Z is a branched or linear organosiloxane moiety having the molecular formula:

—$CH_2$—[$Si(R^a)_2O]_q$—$Si(R^a)_3$ in which each $R^a$ is independently selected from $C_{1-8}$-linear or branched alkyl, vinyl, allyl, aryl, aryl-$C_{1-4}$-alkyl, $C_{1-6}$ alkoxy, $C_{3-6}$-alkenyloxy and $C_{3-6}$-alkylideneaminoxyl, with the proviso that at least one $R^a$ is selected from $C_{1-6}$ alkoxy, $C_{3-6}$-alkenyloxy and $C_{3-6}$-alkylideneaminoxyl. In an embodiment, $R^a$ is selected from the group consisting of $C_{1-8}$-linear or branched alkyl, vinyl, allyl, $C_{1-6}$ alkoxy and $C_{3-6}$-alkenyloxy, such as from the group consisting of $C_{1-6}$ alkoxy and $C_{3-6}$-alkenyloxy. In a preferred embodiment, $R^a$ is $C_{1-6}$ alkoxy, such as $C_{1-2}$ alkoxy. Suitably, —Z is —$CH_2$—$Si(OCH_3)_3$. Preferably, —Z is a linear organosiloxane moiety. In the definition of —Z, q is an integer from 0-5 inclusive; suitably q is 1 or 0.

In one preferred embodiment, Z is defined by the structure

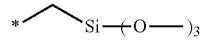

In another preferred embodiment, Z is defined by the structure

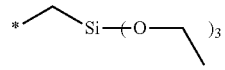

In one embodiment, the organofunctional silane used as starting material for the preparation of the group (-Q-X—Z) is an epoxysilane. In one preferred embodiment, the organofunctional silane used as starting material for the preparation of the group (-Q-X—Z) is an epoxysilane of the type [3-(Glycidyloxy)propyl]trimethoxysilane.

In an embodiment, said organofunctional silane is selected from the group consisting of:
KBM-303: [2-(3,4-Epoxycyclohexyl)ethyl]trimethoxysilane (ShinEtsu, Japan); KBM-403;
[3-(Glycidyloxy)propyl]trimethoxysilane (ShinEtsu, Japan);
KBE-402: [3-(Glycidyloxy)propyl]methyldiethoxysilane (ShinEtsu, Japan);
KBE-403: [3-(Glycidyoxy)propyl]triethoxysilane (ShinEtsu, Japan);
Silquest A-186: [2-(3,4-Epoxycyclohexyl)ethyl] trimethoxysilane, (Momentive, USA);
Silquest A-187: [3-(Glycidyloxy)propyl]trimethoxysilane, (Momentive, USA);
CoatOSil 1770: [2-(3,4-Epoxycyclohexyl)ethyl]triethoxysilane, (Momentive, USA);
Silquest A-Link 25: 3-(Triethoxysilyl)propyl isocyanate, (Momentive, USA);
Silquest A-Link 35: 3-(Trimethoxysilyl)propyl isocyanate, (Momentive, USA);
Dynasylan GLYMO: [3-(Glycidyloxy)propyl]trimethoxysilane, (Evonik, Germany);

In an embodiment, the tie-coat composition comprises 0.1-60%, or 0.1-50%, such as 0.1-45%, e.g. 4.5-40%, by wet weight of the amino-silane adduct of formula (I).

In one preferred embodiment, the HMWA is simultaneously reacted with the organosilane and a substoichiometric amount of an epoxy-functional resin of the type described in the section "epoxy based binder system". Suitable epoxy functional resins which e.g. include bisphenol A based epoxy resins, Bisphenol F based epoxy resins and epoxy resins of the novolac type.

In another embodiment, the HMWA is prepared in a two-step reaction, where the HMWA is reacted with reacted with the organosilane and a substoichiometric amount of an epoxy-functional resin of the type described in the section "epoxy based binder system" in two separate steps. Suitable epoxy functional resins which e.g. include bisphenol A based epoxy resins, Bisphenol F based epoxy resins and epoxy resins of the novolac type.

The amino-silane adduct has a weight average molecular weight in the range of 500-20000 g/mol; suitably in the range of 1000-16000 g/mol, more suitably in the range of 2000-14000 g/mol, even more suitably in the range of 2500-14000 g/mol as measured according to the method herein. Other suitable ranges includes 5000-14000 g/mol, such as 8000-12000 g/mol or 5000-10000 g/mol, such as 5000-8000 g/mol. In some variants, 1000-8000 g/mol, such as 2000-7000 g/mol, even 2000-5000 g/mol.

On porous surfaces, such as aged fouling-release, silanes of molecular weight below 500 g/mol. have a tendency to migrate from the tiecoat into the surface before the silane is chemically bonded in tiecoat binder, thus lowering the concentration in the surface of the tiecoat. This leads to impaired topcoat adhesion.

On porous surfaces, such as aged antifouling, silanes of molecular weight below 500 g/mol. have a tendency to migrate from the tiecoat into the surface before the silane is chemically bonded in tiecoat binder, thus lowering the concentration in the surface of the tiecoat. This leads to impaired topcoat adhesion.

Aminosilanes above 500 g/mol will have less mobility in the tiecoat, and thus lower tendency to migrate into the surface.

Synthesis of HMWA-$\{N(Y)—H\}_p$

Phenalkamines are one example of a HMWA-$\{N(Y)—H\}_p$ type structure. Phenalkamines are essentially Mannich bases formed by the Mannich reaction of an amine, formaldehyde and cardanol. Cardanol is a phenol substituted at the meta position with an unsaturated $C_{15}$ carbon chain. Depending on the stoichiometry of the reaction components, different products can be formed. Mannich bases useful in the present invention can also be prepared from e.g. phenol, t-butyl phenol, Bisphenol A and nonyl phenol.

A proposed Mannich reaction between cardanol, formaldehyde and ethylene diamine (EDA) is shown below as an example of synthesis of HMWA-$\{N(Y)—H\}_p$ (Scheme 1).

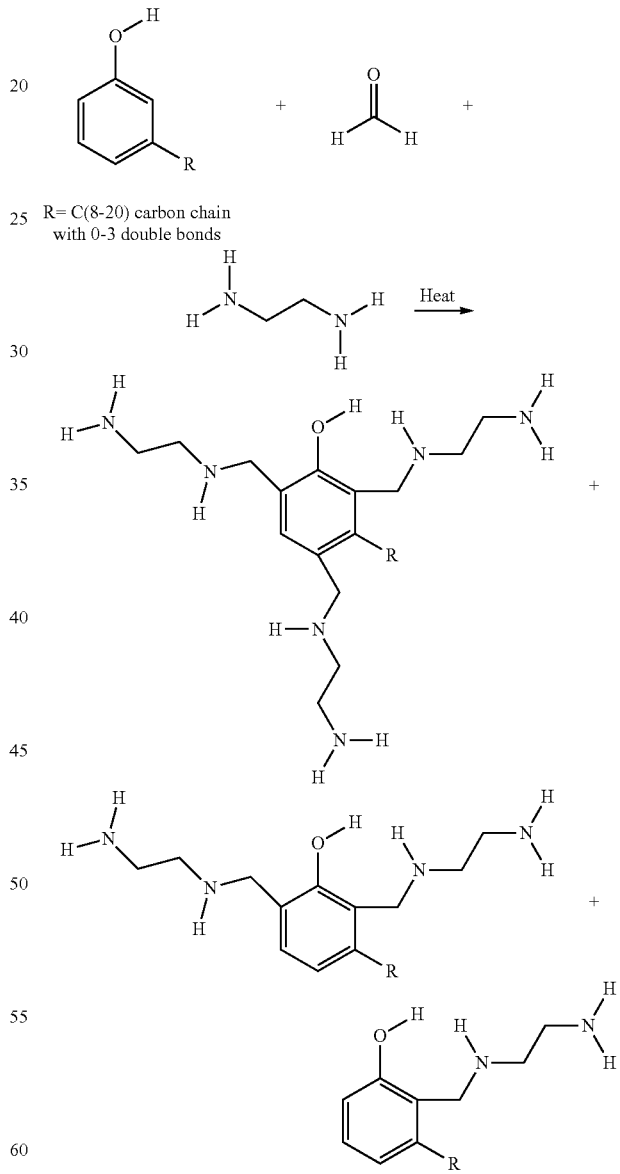

The reaction is performed with heat and removal of the formed water by distillation. The products formed is determined by the individual ratios of substituted phenol (cardanol in this example), formaldehyde and polyamine (ethylene diamine in this example). Formation of higher molecular weight Mannich bases is achieved by reducing the polyamine/formaldehyde ratio and structures as seen in Scheme 2 are obtained. The structures can also be branched on all three diamine moieties.

Scheme 2

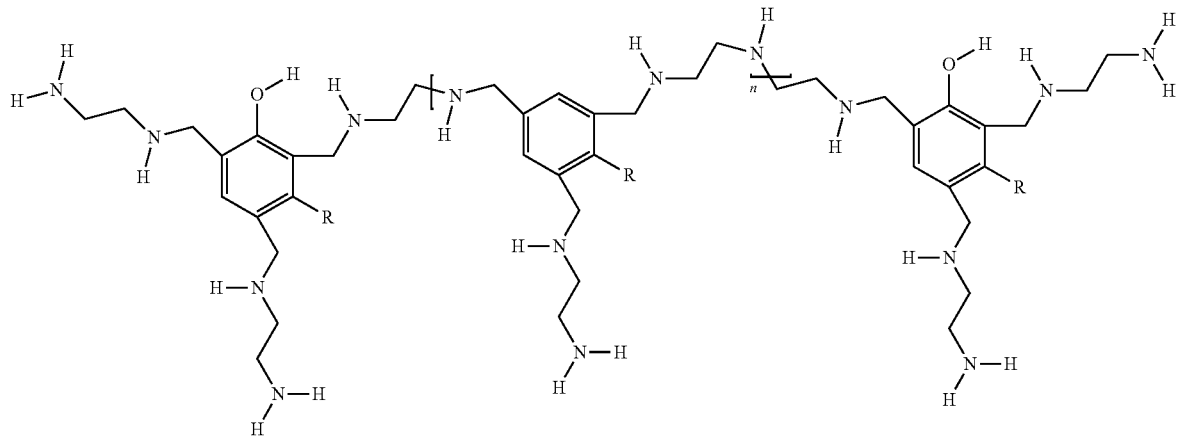

A High Molecular Weight Amine may alternatively be provided by reacting an amino-functional resin (preferably a polyamine) with a sub-stoichiometric amount of an epoxy-functional resin or epoxy functional reactive diluent to form a HMWA constituent. A generic example of this is the reaction of 1,3-cyclohexanebis(methylamine), BAC, (with 4 reactive hydrogens per molecule) with an epoxy. A 1:1 by weight mixture of bisphenol A epoxy with 2 reactive epoxy groups per molecule and a novolac epoxy, with an average of 3.6 reactive epoxy groups per molecule serves as example here. The reaction is preferably performed in a solvent to reduce the viscosity. An epoxy:hydrogen ratio is chosen experimentally with the aim at obtaining an adduct, which has a workable viscosity in solution, preferably below 50000 cSt. Practically, this epoxy:hydrogen ratio is in the range 1:100 to 15:100, more preferably 2:100 to 10:100 depending on the epoxy and amine raw materials. When the reaction is completed, practically all epoxy groups will have reacted and a high molecular weight amine of the generic structure HMWA-$\{N(Y)-H\}_p$ will have formed.

Preparation of Amino-Silane Adduct

The amine of formula HMWA-$\{N(Y)-H\}_p$ described above is further reacted with substoichiometric amount of organofunctional silane to obtain a high molecular weight aminosilane adduct. A organofunctional silane is a silane, which has an organic functional group in the molecule, and at least one hydrolysable group bonded directly to the silicon atom. Usually, the organofunctional silanes have only one silicon atom in the molecule, but some silanes are available with multiple silicon atoms.

A generic structure of the organofunctional silane is outlined below (formula III)

$$Q'-X-CH_2-[Si(R^a)_2O]_q-Si(R^a)_3 \quad (III)$$

—X— is a linker moiety selected from $C_{1-6}$-alkylene which may be optionally substituted with one or more substituents selected from hydroxyl and $C_1$-$C_4$ alkyl; —(CO)—; —NR*—; —O—; —NR*—C(=O)—NR*—; —NR*—C(=O)—; —C(=O)—NR*; -arylene; and combinations thereof, in which R* is selected from H and $C_{1-6}$-alkyl. Suitably, X is $C_{1-6}$-alkylene. Included in this definition are linker moieties X in which X is a poly(alkylether), polyamine, polyamide or polyurea linker moiety. Each $R^a$ is independently selected from $C_{1-8}$-linear or branched alkyl, vinyl, allyl, aryl, aryl-$C_{1-4}$-alkyl, $C_{1-6}$ alkoxy, $C_{3-6}$-alkenyloxy and $C_{3-6}$-alkylideneaminoxyl, with the proviso that at least one $R^a$ is selected from $C_{1-6}$ alkoxy, $C_{3-6}$-alkenyloxy and $C_{3-6}$-alkylideneaminoxyl. Suitably, $R^a$ is selected from —(OCH$_3$). q is an integer from 0-5 inclusive; suitably q is 1 or 0. Q' is an organic functional group capable of reaction with a primary or secondary amine to form -Q- as defined in formula I. Preferably Q' is an epoxide group.

The functionality of the organic moiety (Q' in formula III) on the silane should be chosen in order to be capable of reacting with an available hydrogen on HMWA-$\{N(Y)-H\}_p$ where Y is hydrogen. The silane is thus covalently bonded to HMWA-$\{N(Y)-H\}_p$, thus forming a high molecular weight aminosilane adduct of formula (I). Examples of such organic moieties include epoxy, isocyanate, α,β-unsaturated ester, α,β-unsaturated amide and SILQUEST A-186:

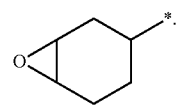

Examples of useful organofunctional silanes which are commercially available include:

KBM-303; [2-(3,4-Epoxycyclohexyl)ethyl]trimethoxysilane; ex. ShinEtsu, Japan

KBM-403; [3-(Glycidyloxy)propyl]trimethoxysilane; ex. ShinEtsu, Japan

KBE-402; [3-(Glycidyloxy)propyl]methyldiethoxysilane; ex. ShinEtsu, Japan

KBE-403; [3-(Glycidyoxy)propyl]triethoxysilane; ex. ShinEtsu, Japan

Silquest A-186; [2-(3,4-Epoxycyclohexyl)ethyl]trimethoxysilane, ex. Momentive, USA Silquest A-187; [3-(Glycidyloxy)propyl]trimethoxysilane, ex. Momentive, USA CoatOSil 1770; [2-(3,4-Epoxycyclohexyl)ethyl]triethoxysilane, ex. Momentive, USA Silquest A-Link 25; 3-(Triethoxysilyl)propyl isocyanate, ex. Momentive, USA Silquest A-Link 35; 3-(Trimethoxysilyl)propyl isocyanate, ex. Momentive, USA Dynasylan GLYMO; [3-(Glycidyloxy)propyl]trimethoxysilane, ex. Evonik, Germany Suitably, the tie-coat composition comprises 0.1-60%, or 0.1-50%, such as 0.1-45%, e.g. 4.5-40%, by wet weight of the amino-silane adduct of formula (I).

The high molecular weight aminosilane adduct may optionally be prepared from an adduct derived from a reaction between the high molecular weight amine and an epoxy resin, such as the one described in the section "epoxy based binder system". This can be pre-reacted to the high molecular weight amine before reaction with the organofunctional silane, or it can be made in one single process, where the epoxy resin is allowed to react with the high molecular weight amine at the same time as the organofunctional silane. Suitable epoxy functional resins include bisphenol A based epoxy resins, Bisphenol F based epoxy resins and epoxy resins of the novolac type.

According to the first and second aspects of the invention, each method comprises the step of: subsequently applying a fouling-release top-coat. The fouling-release top-coat can be established by any conventional condensation curable siloxane containing fouling-release coating composition. The fouling-release top-coat is suitably a condensation curable polysiloxane-based coating. Alternatively, the fouling-release coating is a copolymer comprising a condensation curable siloxane termination. In one embodiment, the polysiloxane-based coating composition comprises a condensation curable polydimethylsiloxane. Examples hereof are a two-component condensation-curing top-coat based on a silanol terminated polydiorganosiloxane which is cross-linked with a silane comprising a hydrolysable group, or a single-component moisture-curable top-coat based on a polydiorganosiloxane with alkoxy reactivity on the terminal groups of the binder.

Alternatively, the fouling-release top-coat may be established using a composition comprising a fluorinated resin in combination with polysiloxanes, e.g. 50-95% of a fluoropolymer and 5-50% of a polysiloxane. Such fluorinated resins are, e.g., disclosed in WO 01/094446 or WO 02/074870. When used alone, the fluorinated resin typically includes functional groups that are capable of reacting with functional groups, e.g. hydroxy groups.

The top-coat is typically applied in a dry film thickness of 20-500 μm, such as 20-400 μm, e.g. 50-300 μm.

The fouling-release top-coat is suitably applied directly to the tie-coat of the invention, meaning that steps (a) and (b) take place directly after one another. However, the methods include instances in which intermediate layers are included, either prior to step (a) (i.e. an intermediate layer is applied between the anticorrosive coat and the tie-coat of the invention), between steps (a) and (b) (i.e. intermediate layer(s) is (are) applied between the tie-coat of the invention and the fouling-release top-coat) or after step (b) (i.e. additional top-coat(s) is (are) applied above the fouling-release top-coat).

In particular, according to the second aspect of the invention, a condensation-curing tie-coat is present between the tie-coat of the invention and a fouling-release top-coat. A condensation-curing tie-coat can have either single- or multiple component(s). A single component composition is curable upon contact with moisture, whereas a multiple component composition (typically two or three components) requires a crosslinker/curing agent to form a crosslinked network.

Further examples of condensation curable terminal groups on a fouling-release top-coat or condensation-curing tie coat include:

—Si(R$^a$)$_3$,

Where each R$^a$ is independently selected from C$_{1-8}$-linear or branched alkyl, vinyl, allyl, aryl, aryl-C$_{1-4}$-alkyl, C$_{1-6}$ alkoxy, C$_{3-6}$-alkenyloxy and C$_{3-6}$-alkylideneaminoxyl, with the proviso that at least one R$^a$ is selected from C$_{1-6}$ alkoxy, C$_{3-6}$-alkenyloxy and C$_{3-6}$-alkylideneaminoxyl. Suitably, R$^a$ is selected from methoxy or methylethylaminoxyl groups.

Alternatively, the top- or intermediate coating composition may comprise a copolymer with condensation curable terminal groups, such as those described in WO 13/000479. Additional Constituents of the Tie-Coat Composition As a water-scavenger, the tie-coat composition may additionally comprise one or more alkyloxysilanes of the formula (II):

Si(R$^b$)$_v$(OR$^c$)$_{4-v}$     (II)

wherein R$^b$, and R$^c$ are as defined in claim 1 for R$^a$ and v is 1, 2 or 3.

Commercially available examples of useful alkyloxysilanes include

Dynasylan VTMO; vinyltrimethoxysilane; ex. Evonik, Germany

Dynasylan MTMS; methyltrimethoxysilane; ex. Evonik, Germany

Silane A 171; vinyltrimethoxysilane; ex. Momentive, USA

Silquest A 1630; methyltrimethoxysilane; ex. Momentive, USA

The tie-coat composition may additionally comprise a condensation catalyst to accelerate the cross-linking. Examples of suitable catalysts include organometal- and metal salts of organic carboxylic acids, such as dibutyl tin dilaurate, dibutyl tin diacetate, dibutyl tin dioctoate, dibutyl tin 2-ethylhexoate, dioctyl tin dilaurate, dioctyl tin diacetate, dioctyl tin dioctoate, dioctyl tin 2-ethylhexoate, dioctyltin di neodecanoate, tin naphthenate, tin butyrate, tin oleate, tin caprylate, iron 2-ethylhexoate, lead 2-ethyloctoate, cobalt-2-ethylhexoate, manganese 2-ethylhexoate, zinc 2-ethylhexoate, zinc naphthenate, zinc stearate, cobalt naphthenate and titanium naphtenate; catalysts containing tertiary amines such as guanidine derivatives, such as 1,2-dicyclohexyl-3-(1-piperidyl)guanidine (FR2930778); 1-butyl-2,3-dicyclohexyl-1,3-dimethylguanidine (WO2010149869) and further tertiary amines, such as 1,4-ethylenepiperazine (DABCO) and 2,4,6-tris(dimethylamino methyl) phenol.

The catalyst may be used alone or as combination of two or more catalysts. The amount of catalyst to be used depends on the reactivity of the catalyst and the cross-linker(s) and desired recoating interval to subsequent coat/drying time. In a preferred embodiment the catalyst concentration is between 0.01-10% by weight; such as 0.01-4%; such as 0.005-2%; especially 0.001-1% of the total combined amount of the epoxy-based binder system and curing agent.

The tie-coat composition may further comprise solvents and additives.

Examples of solvents are alcohols, such as methanol, ethanol, propanol and butanol, aliphatic, cycloaliphatic and aromatic hydrocarbons such as white spirit, cyclohexane, toluene, xylene and naphtha solvent, esters such as methoxypropyl acetate, n-butyl acetate and 2-ethoxyethyl acetate; octamethyltrisiloxane, and mixtures thereof.

The solvents, if any, typically constitute 5-50% by volume of the tie-coat composition.

Examples of additives are:
(i) non-reactive fluids such as organopolysiloxanes; for example polydimethylsiloxane, methylphenyl polysiloxane; petroleum oils and combinations thereof;
(ii) surfactants such as derivatives of propylene oxide or ethylene oxide such as alkylphenol-ethylene oxide condensates (alkylphenol ethoxylates); ethoxylated monoethanolamides of unsaturated fatty acids such as ethoxylated monoethanolamides of linoleic acid; sodium dodecyl sulfate; and soya lecithin;
(iii) wetting agents and dispersants such as those described in M. Ash and I. Ash, "Handbook of Paint and Coating Raw Materials, Vol. 1", 1996, Gower Publ. Ltd., Great Britain, pp 821-823 and 849-851;
(iv) thickeners and anti-settling agents such as colloidal silica, hydrated aluminium silicate (bentonite), aluminiumtristearate, aluminiummonostearate, xanthan gum, chrysotile, pyrogenic silica, hydrogenated castor oil, organomodified clays, polyamide waxes and polyethylene waxes; and
(v) dyes such as 1,4-bis(butylamino)anthraquinone and other anthraquinone derivatives; toluidine dyes, etc.

Any additives typically constitute 0-30%, such as 0-15%, by dry weight of the tie-coat composition.

Furthermore, the tie-coat composition may comprise pigments and fillers.

Pigments and fillers are in the present context viewed in conjunction as constituents that may be added to the tie-coat composition with only limited implications on the adhesion properties. "Pigments" are normally characterised in that they render the final tie-coat composition non-transparent and non-translucent, whereas "fillers" normally are characterised in that they do not render the tie-coat composition non-translucent and therefore do not contribute significantly to hide any material below the coated composition.

Examples of pigments are grades of titanium dioxide, red iron oxide, zinc oxide, carbon black, graphite, yellow iron oxide, red molybdate, yellow molybdate, zinc sulfide, antimony oxide, sodium aluminium sulfosilicates, quinacridones, phthalocyanine blue, phthalocyanine green, black iron oxide, indanthrone blue, cobalt aluminium oxide, carbazole dioxazine, chromium oxide, isoindoline orange, bis-acetoacet-o-tolidiole, benz-imidazolon, quinaphtalone yellow, isoindoline yellow, tetrachloroisoindolinone and quinophthalone yellow.

Examples of fillers are calcium carbonate such as calcite, dolomite, talc, mica, feldspar, barium sulfate, kaolin, nephelin, silica, perlite, magnesium oxide, and quartz flour, etc. Fillers (and pigments) may also be added in the form of nanotubes or fibres, thus, apart from the before-mentioned examples of fillers, the tie-coat composition may also comprise fibres, e.g. those generally and specifically described in WO 00/77102 which is hereby incorporated by reference.

Any pigments and/or fillers typically constitute 0-60%, such as 0-50%, preferably 5-45%, such as 5-40% or 5-35%, by dry weight of the tie-coat composition.

With the aim of facilitating easy application of the tie-coat composition (e.g. by spray, brush or roller application techniques), the tie-coat composition typically has a viscosity in the range of 25-25,000 mPa·s, such as in the range of 150-15,000 mPa·s, in particular in the range of 200-4000 mPa·s.

Preparation of the Tie-Coat Composition

The tie-coat composition may be prepared by any suitable technique that is commonly used within the field of paint production. Thus, the various constituents may be mixed together utilizing a mixer, a high speed disperser, a ball mill, a pearl mill, a grinder, a three-roll mill etc. The tie-coat compositions are typically prepared and shipped as two- or three-component systems that should be combined and thoroughly mixed immediately prior to use. The paints according to the invention may be filtered using bag filters, patron filters, wire gap filters, wedge wire filters, metal edge filters, EGLM turnoclean filters (ex. Cuno), DELTA strain filters (ex. Cuno), and Jenag Strainer filters (ex. Jenag), or by vibration filtration. An example of a suitable preparation method is described in the Examples.

The tie-coat composition to be used in the method of the invention is typically prepared by mixing two or more components e.g. two pre-mixtures, one pre-mixture comprising the one or more reactive epoxy binders and one pre-mixture comprising the one or more curing agents.

Additional aspects of the methods of the invention are as follows:

A method is provided for applying a fouling-release coating system to a surface, said method comprising the steps of: (a) applying a tie-coat composition to the surface, wherein said tie-coat composition comprises:
i) a binder system comprising an epoxy resin;
ii) one or more adhesion-promoting agents selected from the group consisting of hydroxy-functional polysiloxanes and $C_{1-4}$-alkoxy-functional polysiloxanes; and
iii) an amino-silane adduct obtained by:
 I. in a first Mannich-type reaction, reacting a $C_{7-20}$-alkyl phenol (in particular cardanol), formaldehyde and one or more amine(s) selected from diamines, triamines and tetraamines, and optionally further reacting with a substoichiometric amount of an epoxy-functional resin to form a HMWA-{N(Y)—H}$_p$ component in which HMWA, Y and p are as defined herein; and
 II. in a second reaction, reacting the HMWA-{N(Y)—H}$_p$ component from the first reaction with an epoxy-silane to form an amino-silane adduct;
wherein the weight average molecular weight of the amino-silane adduct is in the range of 500-20000 g/mol;
and (b) subsequently applying a fouling-release top-coat.

Additionally, a method is provided for applying a fouling-release coating system to a surface, said method comprising the steps of: (a) applying a tie-coat composition to the surface, wherein said tie-coat composition comprises:
i) a binder system comprising an epoxy resin;
ii) optionally, one or more adhesion-promoting agents selected from the group consisting of hydroxy-functional polysiloxanes and $C_{1-4}$-alkoxy-functional polysiloxanes; and
iii) an amino-silane adduct obtained by:
 I. in a first Mannich-type reaction, reacting a $C_{7-20}$-alkyl phenol (in particular cardanol), formaldehyde and one or more amine(s) selected from diamines, triamines and tetraamines, and optionally further reacting with a substoichiometric amount of an epoxy-functional resin to form a HMWA-{N(Y)—H}$_p$ component in which HMWA, Y and p are as defined herein; and
 II. in a second reaction, reacting the HMWA-{N(Y)—H}$_p$ component from the first reaction with an epoxy-silane to form an amino-silane adduct;

wherein the weight average molecular weight of the amino-silane adduct is in the range of 500-20000 g/mol;
(b) applying a condensation-curing tie-coat to the tie-coat of step (a); and (c) subsequently applying a fouling-release top-coat.

A method is also provided for applying a fouling-release coating system to a surface (which is preferably an anticorrosive coat), said method comprising the steps of: (a) applying a tie-coat composition to the surface, wherein said tie-coat composition comprises:
  i) a binder system comprising an epoxy resin;
  ii) one or more adhesion-promoting agents selected from the group consisting of hydroxy-functional polysiloxanes and $C_{1-4}$-alkoxy-functional polysiloxanes; and
  iii) an amino-silane adduct obtained by:
    I. in a first reaction, reacting an amino-functional resin (preferably a polyamine) with a substoichiometric amount of an epoxy-functional resin or epoxy functional reactive diluent to form a HMWA-{N(Y)—H}$_p$ component, in which HMWA, Y and p are as defined herein,
    II. in a second reaction, reacting the HMWA-{N(Y)—H}$_p$ component from the first reaction with an epoxy-silane to form an amino-silane adduct;
  wherein the weight average molecular weight of the amino-silane adduct is in the range of 500-20000 g/mol;
and (b) subsequently applying a fouling-release top-coat.

A method is also provided for applying a fouling-release coating system to a surface (which is preferably an anticorrosive coat), said method comprising the steps of: (a) applying a tie-coat composition to the surface, wherein said tie-coat composition comprises:
  i) a binder system comprising an epoxy resin;
  ii) optionally, one or more adhesion-promoting agents selected from the group consisting of hydroxy-functional polysiloxanes and $C_{1-4}$-alkoxy-functional polysiloxanes; and
  iii) an amino-silane adduct obtained by:
    I. in a first reaction, reacting an amino-functional resin (preferably a polyamine) with a substoichiometric amount of an epoxy-functional resin or epoxy functional reactive diluent to form a HMWA-{N(Y)—H}$_p$ component, in which HMWA, Y and p are as defined herein,
    II. in a second reaction, reacting the HMWA-{N(Y)—H}$_p$ component from the first reaction with an epoxy-silane to form an amino-silane adduct;
  wherein the weight average molecular weight of the amino-silane adduct is in the range of 500-20000 g/mol;
(b) applying a condensation-curing tie-coat to the tie-coat of step (a); and (c) subsequently applying a fouling-release top-coat.

In these additional aspects of the method of the invention, all details of the amino-silane adduct are as per the method of the first embodiment set out above. In addition, preferred features of the amino-silane adduct may be combined as desired, to provide more preferred embodiments of the invention.

Coated Article

In another embodiment, the invention provides an article comprising a substrate, said substrate having a surface, and a tie-coat on said surface, wherein the tie-coat is prepared from a tie-coat composition, said tie-coat composition comprising:
  i) a binder system comprising an epoxy resin;
  ii) one or more adhesion-promoting agents selected from the group consisting of hydroxy-functional polysiloxanes, and $C_{1-4}$-alkoxy-functional polysiloxanes, and;
  iii) an amino-silane adduct of the formula I:

HMWA-N(Y)-Q-X—Z                                         (I)

in which HMWA, —N(Y)—, Q, X and Z are as described above.

In another aspect, the invention provides an article comprising a substrate, said substrate having a surface and a first tie-coat on said surface, wherein the first tie-coat is prepared from a tie-coat composition, said tie-coat composition comprising:
  i) a binder system comprising an epoxy resin;
  ii) optionally, one or more adhesion-promoting agents selected from the group consisting of hydroxy-functional polysiloxanes, and $C_{1-4}$-alkoxy-functional polysiloxanes, and;
  iii) an amino-silane adduct of the formula I:

HMWA-N(Y)-Q-X—Z                                         (I)

in which HMWA, —N(Y)—, Q, X and Z are as described above, and in which said article additionally comprises a condensation-curing tie-coat on said first tie-coat.

In either aspect, the article according to the invention preferably comprises a fouling-release coating on said tie-coat(s); i.e. the surface is defined by a fouling-release coating. The fouling-release top-coat may be any such top-coat disclosed herein. The substrate typically comprises a metal such as steel, iron, aluminium, or a glass-fibre.

Additionally, in either aspect, an anticorrosive coat is preferably present on at least a part of the surface of said substrate and the tie-coat composition/first tie-coat composition is coated on said anticorrosive coat.

Curing Agent Composition

In another embodiment, the invention provides a curing agent composition. In a first aspect of this embodiment, the curing agent composition comprises an amino-silane adduct of the formula (Ia) or (Ib):

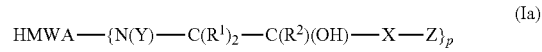

HMWA—{N(Y)—C(R$^1$)$_2$—C(R$^2$)(OH)—X—Z}$_p$          (Ia)

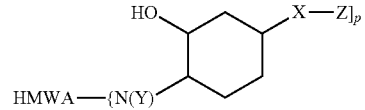

(Ib)

The curing agent composition preferably comprises an amino-silane adduct of the formula (Ia).

In formulae Ia and Ib, HMWA-{N(Y)—}$_p$ is a moiety comprising three or more amino groups, at least some of which are primary or secondary amino groups; wherein each —N(Y)— is a secondary or tertiary amine, wherein Y is selected from hydrogen and $C_{1-4}$-alkyl; wherein said HMWA moiety comprises at least one phenolic moiety and at least one $C_{7-20}$-aliphatic moiety. The at least one $C_{7-20}$-aliphatic moiety may e.g. independently be selected from —(CH$_2$)$_7$CH=CH(CH$_2$)$_5$CH$_3$, —(CH$_2$)$_7$CH=CHCH$_2$CH=CH(CH$_2$)$_2$CH$_3$, and —(CH$_2$)$_7$CH=CHCH$_2$CH=CHCH$_2$CH=CH$_2$. The HMWA-{N(Y)—}$_p$ moiety may be the Mannich condensation reaction product of a $C_{7-20}$-alkyl phenol (in particular cardanol), formaldehyde and one or more amine(s) selected from diamines, triamines or tetraamines, optionally further reacted with a substoichiometric amount of an epoxy-functional resin.

In formulae Ia, each $R^1$ and $R^2$ are independently selected from hydrogen and $C_{1-4}$-alkyl, and are preferably both hydrogen.

In formulae Ia and Ib, p is 1-20, preferably 1-15.

In formulae Ia and Ib, —X— is a linker moiety selected from $C_{1-6}$-alkylene which may be optionally substituted with one or more substituents selected from $C_1$-$C_4$ alkyl; —O—; and combinations thereof. Suitably, X is $C_{1-6}$-alkylene. Included in this definition are linker moieties X in which X is a poly(alkylether) linker moiety.

In formulae Ia and Ib, —Z— is a branched or linear organosiloxane moiety having the molecular formula:

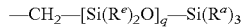

—$CH_2$—[Si($R^e$)$_2$O]$_q$—Si($R^a$)$_3$ in which each $R^a$ is independently selected from $C_{1-8}$-linear or branched alkyl, vinyl, allyl, aryl, aryl-$C_{1-4}$-alkyl, $C_{1-6}$ alkoxy, $C_{3-6}$-alkenyloxy and $C_{3-6}$-alkylideneaminoxyl, with the proviso that at least one $R^a$ is selected from $C_{1-6}$ alkoxy, $C_{3-6}$-alkenyloxy and $C_{3-6}$-alkylideneaminoxyl. Suitably, —Z is —$CH_2$—Si($OCH_3$)$_3$.

In formulae Ia and Ib, q is an integer from 0-5 inclusive; suitably q is 1 or 0.

wherein the weight average molecular weight of the amino-silane adduct is in the range of 500-20000 g/mol.

The amino-silane adducts of formulae Ia and Ib, have a weight average molecular weight in the range of 500-20000 g/mol; suitably in the range of 1000-16000 g/mol, more suitably in the range of 2000-14000 g/mol, even more suitably in the range of 2500-14000 g/mol as measured according to the method herein.

In another aspect, a curing agent composition is provided which comprises an amino-silane adduct obtained by:
I. in a first Mannich-type reaction, reacting a $C_{7-20}$-alkyl phenol (in particular cardanol), formaldehyde and one or more amine(s) selected from diamines, triamines and tetraamines, and optionally further reacting with a substoichiometric amount of an epoxy-functional resin to form a HMWA-{N(Y)—H}$_p$ component in which HMWA, Y and p are as defined herein; and
II. in a second reaction, reacting the HMWA-{N(Y)—H}$_p$ component from the first reaction with an epoxy-silane to form an amino-silane adduct;
wherein the weight average molecular weight of the amino-silane adduct is in the range of 500-20000 g/mol, more suitably in the range of 2000-15000 g/mol.

A curing agent composition comprising an amino-silane adduct, may also be obtained by:
I. in a first reaction, reacting an amino-functional resin (preferably a polyamine) with a substoichiometric amount of an epoxy-functional resin or epoxy functional reactive diluent to form a HMWA-{N(Y)—H}$_p$ component in which HMWA, Y and p are as defined herein,
II. in a second reaction, reacting the HMWA-{N(Y)—H}$_p$ component from the first reaction with an epoxy-silane to form an amino-silane adduct;
wherein the weight average molecular weight of the amino-silane adduct is in the range of 500-20000 g/mol, more suitably in the range of 2000-15000 g/mol.

The present invention provides a tie-coat composition comprising the curing agent compositions described above. The tie-coat compositions are particularly useful in connection with fouling-release coating systems. The invention also provides a tie-coat composition per se comprising the curing agent according to the invention. All details of the curing agent of the invention are also relevant to the tie-coat composition.

EXAMPLES

Materials

| Product | Supplier | Description | Nomenclature in examples |
|---|---|---|---|
| Araldite ® GZ 7071 X 75 | Huntsman Advanced Materials, Switzerland | Solid bisphenol A epoxy in xylene | BPA-Epoxy 1 |
| n-butanol, technical grade | Local supplier | — | Butanol |
| xylene, technical grade | Local supplier | — | Xylene |
| Dynasylan DAMO-T | Evonik Industries, Germany | 3-(2-aminoethylamino)propyltrimethoxysilane | Aminosilane |
| Dynasylan GLYMO | Evonik Industries, Germany | Gamma glycidoxypropyl trimethoxysilane | Epoxysilane |
| Xiameter ® PMX-0156 Silanol Fluid | Xiameter | Silanol terminated polysiloxane | Adhesion promoter |
| Araldite ® GY 250 | Huntsman Advanced Materials, Switzerland | Bisphenol A-diglycidyl ether, average molecular weight 700 g/mol | BPA-Epoxy 2 |
| NC-541-X-90 | Cardolite Corporation, United States | Mannich base (high molecular weight amine obtained by a mannich base reaction of cardanol, formaldehyde and ethylenediamine) | Mannich base 1 |
| Dynasylan VTMO | Evonik Industries, Germany | Vinyltrimethoxysilane | Vinyltrimethoxysilane |
| 1,3-Cyclohexanebis(methylamine) | Sigma-Aldrich ® Denmark | 1,3-Cyclohexanebis(methylamine), mixture of isomers | 1,3-BAC |
| Methanol, technical grade | Local supplier | — | Methanol |
| Araldite ® EPN 1180 X 80 | Huntsman Advanced Materials, Switzerland | Semi-solid Epoxy Phenolic Novolac | Novolac epoxy |
| Cardolite ® Lite 2002 | Cardolite Corporation, United States | Mannich base (high molecular weight amine obtained by a mannich base reaction of cardanol, formaldehyde, MXDA and TEPA) | Mannich base 2 |

| Product | Supplier | Description | Nomenclature in examples |
|---|---|---|---|
| Crayamid 147 | Arkema, India | Polyaminoamide | Polyaminoamide |
| Cardolite ® NX5454 | Cardolite Corporation, United States | Mannich base (high molecular weight amine obtained by a mannich base reaction of cardanol, formaldehyde and MXDA) | Mannich base 3 |
| Laroflex MP 25 | BASF - Germany | Vinyl resin | Vinyl resin |
| 15570-50630 | Hempel A/S, Denmark | HEMPADUR 15570, Epoxy primer, (mixed formulation) | 15570-50630 |
| 45551-11630 | Hempel A/S, Denmark | Hempel's Light Primer, Epoxy primer (mixed formulation) | 45551-11630 |
| 15579-50630 | Hempel A/S, Denmark | HEMPADUR 15570, Epoxy primer (component 1, epoxy base) | 15579-50630 |
| 87500-59151 | Hempel A/S, Denmark | Hempasil X3, Silicone based fouling release topcoat (mixed formulation) | 87500-59151 |
| 8190N-62900 | Hempel A/S, Denmark | Hempel's Antifouling Globic NCT | 8190N-62900 |
| 27500-23410 | Hempel A/S, Denmark | Hempasil Nexus X-Tend | 27500-23410 |
| Intersleek 737 (Pink) | International Paint | Intersleek ® 737, Silicone elastomer tie coat (mixed formulation) | IS-737 |
| Intersleek 970 (Red) | International Paint | Intersleek ® 970, Fluoropolymer Foul Release Coating (mixed formulation) | IS-970 |
| Intersleek 757 (Grey) | International Paint | Intersleek ® 757, Silicone elastomer Foul Release Coating (mixed formulation) | IS-757 |

| Product | Supplier | Description | Nomenclature in examples |
|---|---|---|---|
| Kemira X660 | Kemira Pigments OY, Finland | Rutile titanium dioxide | Rutile titanium dioxide |
| Black Iron Oxide 318M | Bayer Germany | Black iron oxide | Black iron oxide |
| Minex S20 | North Cape Nefelin A/S, Norway | Aluminium, potassium, sodium silicate | Extender pigment |
| Crayvallac Super | Arkema, France | Polyamide wax | Rheological agent |
| Gaskamine 240 | Mitsubishi Gas Chemical Co, Japan | m-xylylene diamine styrene adduct | (m-XDA) styrene adduct |
| SIV9280.0 | Gelest Ltd - US | Vinyl oximino silane | VOS |

Preparation of Epoxy Resin Composition (Constituent 1)

The epoxy resin composition comprises the epoxy binder(s) and possible binder extender, plasticizers, fillers, pigments etc. as outlined in the detailed disclosure of the invention. Batches of 750 ml were prepared in a 1000 ml metal can (paint tin).

The paints for the experiments were made using components and amounts (wet weight in gram) as outlined in Table 1 and 1a below

TABLE 1

| | RM. # | | Composition no. 1, 2, 3, 4, 6, 7, 14, 15, 18, 19 | 5, 16, 17 | 8, 10 | 9, 11, 12, 13 | 20, 21 |
|---|---|---|---|---|---|---|---|
| (Epoxy Resin) | 1 | 15579-50630 | | 729.2 | | | |
| | 2 | BPA-Epoxy 1 | 592.1 | | | | |
| | 3 | Butanol | 98.7 | | 109.6 | 50.5 | 52.7 |
| | 4 | Xylene | | | 109.6 | 252.7 | 263.3 |
| | 5 | Adhesion promoter | 59.2 | 20.8 | 65.8 | 30.3 | |

TABLE 1-continued

| | RM. # | | Composition no. 1, 2, 3, 4, 6, 7, 14, 15, 18, 19 | 5, 16, 17 | 8, 10 | 9, 11, 12, 13 | 20, 21 |
|---|---|---|---|---|---|---|---|
| | 6 | BPA-Epoxy 2 | | 464.9 | 214.3 | 223.3 | |
| | 7 | Vinyl resin | | | | 202.2 | 210.7 |
| | Total (Epoxy Resin Composition) | | 750.0 | 750.0 | 750.0 | 750.0 | 750.0 |

TABLE 1a

| | RM. # | Composition no. | 22 | 23, 26, 27, 28, 29 | 24, 25 |
|---|---|---|---|---|---|
| Component 1 (Epoxy Resin Composition) | 1a | Rutile titanium dioxide | 28.4 | 27.8 | 29.0 |
| | 2a | Black iron oxide | 12.0 | 11.8 | 12.3 |
| | 3a | Rheological agent | 4.4 | 4.3 | 4.5 |
| | 4a | Extender pigment | 163.8 | 160.3 | 167.4 |
| | 5a | Butanol | 27.3 | 26.7 | 27.9 |
| | 6a | Xylene | 272.9 | 267.1 | 279.0 |

TABLE 1a-continued

| RM. # | Composition no. | 22 | 23, 26, 27, 28, 29 | 24, 25 |
|---|---|---|---|---|
| 7a | Adhesion promoter | 16.4 | 32.1 | |
| 8a | BPA-Epoxy 2 | 115.7 | 113.2 | 118.3 |
| 9a | Vinyl resin | 109.2 | 106.8 | 111.6 |
| | Total (Epoxy Resin Compositin) | 750.0 | 750.0 | 750.0 |

Compositions 1-4, 6, 7, 14, 15, 18 and 19: Raw materials #2, 3 and 5 are thoroughly mixed on a dissolver until homogeneous. A milky solution is formed. The composition is thoroughly stirred before use, to avoid phase separation.

Composition 5, 16 and 17: A commercial epoxy primer base composition (Raw material #1, 15579-50630 ex. Hempel A/S) is added to adhesion promoter (Raw material #5, Adhesion promoter) and stirred in a dissolver until homogenous.

Composition 8 and 10: Raw materials #3-6 are thoroughly mixed in a dissolver until homogenous. A milky solution is formed. The composition is thoroughly stirred before use, to avoid phase separation.

Composition 9 and 11-13: Raw material #7 (vinyl resin) is dissolved in Raw material #4 (xylene) in a dissolver, and remaining raw materials are added and mixed until homogenous. The mixture is thoroughly stirred before use, to avoid phase separation.

Composition 20 and 21: Raw material #7 (vinyl resin) is dissolved in Raw material #4 (xylene) in a dissolver, and remaining raw materials are added and mixed until homogenous.

Composition 22, 23, 26, 27, 28 and 29: Raw material #9a (vinyl resin) is dissolved in Raw material #6a (xylene) in a dissolver. Remaining raw materials except #7a (adhesion promoter) are added and dispersed until the temperature reach 70° C. When cooled to room temperature, the raw material #7a (adhesion promoter) is added and dispersed until homogenous.

Composition 24 and 25: Prepared in the same manner as 22, 23, 26, 27, 28 and 29, except that the raw material #7a (adhesion promoter) has been omitted.

Preparation of Curing Agents (Constituent 2)

The curing agent is moisture sensitive due to the content of hydrolysable silanes, so to avoid unnecessary reaction with moisture from the atmosphere, the vessel can advantageously be flushed with dry nitrogen. To further prevent moisture entering the reaction vessel during production, the vessel is preferably equipped with a lid or the product is canned immediately after mixing and allowed to react in the can. In the following examples, a metal can with tightly fitting lid (paint tin) has been used as the reaction vessel.

The curing agent can be prepared in a one-step process (all raw materials for the curing agent are mixed together in one reaction vessel/dissolver while stirring) and allowed to react for 1 day at room temperature (25° C.). In some instances, it may be an advantage to prepare the curing agent in more than one step, for example if it is preferred to incorporate an amine which is not reacted with the silane, or if a high molecular weight amine adduct is prepared in a first reaction before reacting the high molecular weight amine adduct with the silane. If step 2 involves a chemical reaction (for example an epoxy/amine addition) it requires a reaction time of 1 day to complete.

750 g of each curing agent were prepared in a 1000 ml paint tin with tightly fitting lid using raw materials and amounts (wet weight in gram) as outlined in Table 2 and Table 2a.

TABLE 2

| | | | | Composition no. | | | | | | | | | | | |
|---|---|---|---|---|---|---|---|---|---|---|---|---|---|---|---|
| | | RM. # | | 1, 10, 11, 20, 22, 23, 24 | 2, 8, 9 | 3 | 4, 5 | 6 | 7 | 12 | 13 | 14, 15, 21, 25, 27 | 16 | 17 | 18, 19 |
| Constituent 2 (Curing Agent) | Step 1 | 1 | Epoxysilane | | | | | | 100.2 | 109.9 | | | | | |
| | | 2 | Vinyltrimethoxy-silane | | | | | | 44.0 | 48.3 | | | 74.2 | | |
| | | 3 | Mannich base 1 | 348.3 | | | | | 328.8 | 360.5 | 348.3 | 438.8 | | | |
| | | 4 | 1,3-BAC | | | | | 256.6 | | | | | | | |
| | | 5 | Methanol | | | | | 49.3 | | | 46.7 | | | | |
| | | 6 | Xylene | 223.9 | 232.6 | 257.1 | 278.7 | 49.3 | 211.0 | 231.3 | 223.9 | 281.9 | 356.2 | 395.3 | 373.4 |
| | | 7 | Mannich base 2 | | 288.9 | | | | | | | | | | |
| | | 8 | Mannich base 3 | | 332.8 | | | | | | | | | | |
| | | 9 | Polyaminoamide | | | | 250.1 | | | | | | 319.6 | 354.7 | 335.1 |
| | | 10 | Novolac epoxy | | | | | 49.3 | | | | | | | |
| | | 11 | BPA-Epoxy 2 | 24.9 | 25.8 | 28.6 | 31.0 | 49.3 | 22.0 | | 24.9 | 29.4 | | | 41.5 |
| | Step 2 | 12 | Epoxysilane | 106.2 | 110.3 | 121.9 | 132.2 | 296.1 | | | 106.2 | | | | |
| | | 13 | Vinyltrimethoxy-silane | 46.7 | 48.5 | 53.6 | 58.1 | | | | | | | | |
| | | 14 | Mannich base 3 | | | | | | 44.0 | | | | | | |
| | | Total (Curing Agent) | | 750.0 | 750.0 | 750.0 | 750.0 | 750.0 | 750.0 | 750.0 | 750.0 | 750.0 | 750.0 | 750.0 | 750.0 |
| | | Weight Average Mw (measured) | | 10400 | 3150 | 2090 | 1100 | 1400 | 10400 | — | — | Non-aminosilane adduct references | | | |

TABLE 2a

| | | RM. # | Composition no. | 29 | 28 | 26 |
|---|---|---|---|---|---|---|
| Component 2 (Curing Agent) | Step 1 | 1a | Epoxysilane | | 106.2 | |
| | | 2a | Vinyltrimethoxysilane | 46.3 | 46.7 | |
| | | 3a | Mannich base 1 | 345.9 | 348.6 | 84.9 |
| | | 4a | 2-(3,4 epoxycyclohexyl) ethyltrimethoxysilane | 111.1 | | |
| | | 5a | (m-XDA) styrene adduct | | | 208.7 |

TABLE 2a-continued

|  | RM. # | Composition no. | 29 | 28 | 26 |
|---|---|---|---|---|---|
|  | 6a | Xylene | 222.0 | 223.7 | 254.7 |
|  | 7a | BPA-Epoxy 2 | 24.7 | 24.9 | 28.3 |
| Step | 8a | Epoxysilane |  |  | 120.3 |
| 2 | 9a | Vinyltrimethoxysilane |  |  | 53.1 |
|  |  | Total (Curing Agent) | 750.0 | 750.0 | 750.0 |

Composition 1-6, 8-11, 13, 20, 22, 23 and 24

The curing agents are prepared in a two-step reaction. A high molecular weight amine adduct is prepared in step 1, followed by reacting the newly formed high molecular weight amine with an epoxy silane. Step 1: Raw materials #1-11 are mixed together in a 1000 ml metal can (paint tin). The can was flushed with nitrogen for 10 seconds and the lid was closed. The can was shaken on a single arm electric paint shaker ex. Red Devil Equipment Co. for 15 minutes and allowed to react for 1 day at room temperature (25° C.). Step 2: The epoxy silane (raw material number 12) and the alkyltrimethoxysilane (vinyltrimethoxysilane raw material number 13) were added. The can was flushed with nitrogen for 10 seconds and the lid was closed. The can was shaken on a single arm electric paint shaker ex. Red Devil Equipment Co. for 15 minutes and allowed to react for 1 day at room temperature (25° C.). The curing agent is ready to use.

Composition 7

The curing agent is prepared in a two-step reaction. A high molecular weight aminosilane adduct is prepared in step 1 followed by addition of a separate amine in step 2. Step 1: Raw materials #1-11 are mixed together in a 1000 ml metal can (paint tin). The can was flushed with nitrogen for 10 seconds and the lid was closed. The can was shaken on a single arm electric paint shaker ex. Red Devil Equipment Co. for 15 minutes and allowed to react for 1 day at room temperature (25° C.). Step 2: The additional amine (raw material number 14) was added. The can was flushed with nitrogen for 10 seconds and the lid was closed. The can was shaken on a single arm electric paint shaker ex. Red Devil Equipment Co. for 15 minutes. The curing agent is ready to use.

Compositions 12, 14-19, 21, 25 and 27:

These curing agents are produced in a one-step reaction. All raw materials (Raw materials #1-11) are mixed together in a 1000 ml metal can (paint tin). The can was flushed with nitrogen for 10 seconds and the lid was closed. The can was shaken on a single arm electric paint shaker ex. Red Devil Equipment Co. for 15 minutes and allowed to react for 1 day at room temperature (25° C.). The curing agent is ready to use.

Composition 29, table 2a: The curing agent is produced in a one-step reaction. All raw materials (Raw materials #2a-#4a and #6a-#7a) are mixed together in a 1000 ml metal can (paint tin). The can was flushed with nitrogen for 10 seconds and the lid was closed. The can was shaken on a single arm electric paint shaker ex. Red Devil Equipment Co. for 15 minutes and allowed to react for 1 day at room temperature (25° C.). The curing agent is ready to use.

Composition 28, table 2a: The curing agent is produced in a one-step reaction. All raw materials (Raw materials #1a-#3a and #6a-#7a) are mixed together in a 1000 ml metal can (paint tin). The can was flushed with nitrogen for 10 seconds and the lid was closed. The can was shaken on a single arm electric paint shaker ex. Red Devil Equipment Co. for 15 minutes and allowed to react for 1 day at room temperature (25° C.). The curing agent is ready to use.

Composition 26, table 2a: The curing agent is prepared in a two-step reaction. A high molecular weight amine adduct is prepared in step 1, followed by reacting the newly formed high molecular weight amine with an epoxy silane. Step 1: Raw materials #3a and #5a-#7a are mixed together in a 1000 ml metal can (paint tin). The can was flushed with nitrogen for 10 seconds and the lid was closed. The can was shaken on a single arm electric paint shaker ex. Red Devil Equipment Co. for 15 minutes and allowed to react for 1 day at room temperature (25° C.). Step 2: The epoxy silane (raw material number #8a) and the alkyltrimethoxysilane (vinyltrimethoxysilane raw material number #9a) were added. The can was flushed with nitrogen for 10 seconds and the lid was closed. The can was shaken on a single arm electric paint shaker ex. Red Devil Equipment Co. for 15 minutes and allowed to react for 1 day at room temperature (25° C.). The curing agent is ready to use.

Additives (Constituent 3)

The additives are used in reference examples 14-19 and 21 and comprise epoxy silane or aminosilane, which are added to the composition just before application. Therefore, these compositions do not comprise a high molecular weight aminosilane adduct.

In table 3a, the additive used in example 24 and reference example 25, is an oxime tipped polydimethyl siloxane formed by reacting 50 g silanol terminated polydimethylsiloxane (Xiameter® PMX-0156 Silanol Fluid) with 20 g vinyl oximino silane SIV9280.0 in a closed 100 ml container flushed with nitrogen and allowed to react for 24 hours at 45° C.

TABLE 3

Tiecoat compositions

| | Composition # | 1 | 2 | 3 | 4 | 5 | 6 | 7 | 8 | 9 | 10 | 11 | 12 | 13 |
|---|---|---|---|---|---|---|---|---|---|---|---|---|---|---|
| Constituent 1 (Epoxy resin compositions) | 15579-50630 |  |  |  |  | 108.4 |  |  |  |  |  |  |  |  |
| | BPA-Epoxy 1 | 30.0 | 30.0 | 30.0 | 30.0 |  | 350.0 | 30.0 |  |  |  |  |  |  |
| | Butanol | 5.0 | 5.0 | 5.0 | 5.0 |  | 58.3 | 5.0 | 2.5 | 2.5 | 2.5 | 2.5 | 2.5 | 2.5 |
| | Xylene |  |  |  |  |  |  |  | 2.5 | 12.5 | 2.5 | 12.5 | 12.5 | 12.5 |
| | Adhesion promoter | 3.0 | 3.0 | 3.0 | 3.0 | 3.1 | 35.0 | 3.0 | 1.5 | 1.5 | 1.5 | 1.5 | 1.5 | 1.5 |
| | BPA-Epoxy 2 |  |  |  |  |  |  |  | 10.6 | 10.6 | 10.6 | 10.6 | 10.6 | 10.6 |
| | Vinyl resin |  |  |  |  |  |  |  |  | 10.0 |  | 10.0 | 10.0 | 10.0 |
| | Total (Constituent 1) | 38.0 | 38.0 | 38.0 | 38.0 | 111.5 | 443.3 | 38.0 | 17.1 | 37.7 | 17.1 | 37.1 | 37.1 | 37.1 |
| Constituent 2 (Curing Agent) Step 1 | Epoxysilane |  |  |  |  |  | 3.4 |  |  |  |  |  | 3.4 |  |
| | Vinyltrimethoxysilane |  |  |  |  |  | 1.5 |  |  |  |  |  | 1.5 |  |
| | Mannich base 1 | 11.2 |  |  |  |  | 11.2 |  |  | 11.2 |  | 11.2 | 11.2 | 11.2 |
| | 1,3-BAC |  |  |  |  |  | 26.0 |  |  |  |  |  |  |  |
| | Methanol |  |  |  |  |  | 5.0 |  |  |  |  |  |  | 1.5 |
| | Xylene | 7.2 | 7.2 | 7.2 | 7.2 | 7.2 | 5.0 | 7.2 | 7.2 | 7.2 | 7.2 | 7.2 | 7.2 | 7.2 |

TABLE 3-continued

Tiecoat compositions

| | | | | | | | | | | | | | | |
|---|---|---|---|---|---|---|---|---|---|---|---|---|---|---|
| | | Mannich base 2 | | | 8.1 | | | | | | | | | |
| | | Mannich base 3 | | 10.3 | | | | | | 10.3 | 10.3 | | | |
| | | Polyaminoamide | | | | 6.5 | 6.5 | | | | | | | |
| | | Novolac epoxy | | | | | | 5.0 | | | | | | |
| | | BPA-Epoxy 2 | 0.8 | 0.8 | 0.8 | 0.8 | 0.8 | 5.0 | 0.8 | 0.8 | 0.8 | 0.8 | 0.8 | 0.8 |
| | Step 2 | Epoxysilane | 3.4 | 3.4 | 3.4 | 3.4 | 3.4 | 30.0 | | 3.4 | 3.4 | 3.4 | 3.4 | 3.4 |
| | | Vinyltrimethoxysilane | 1.5 | 1.5 | 1.5 | 1.5 | 1.5 | | | 1.5 | 1.5 | 1.5 | 1.5 | |
| | | Mannich base 3 | | | | | | | 1.5 | | | | | |
| | | Total (Constituent 2) | 24.1 | 23.2 | 21.0 | 19.4 | 19.4 | 76.0 | 25.6 | 23.2 | 23.2 | 24.1 | 24.1 | 23.3 | 24.1 |
| Constituent 3 | | Aminosilane | | | | | | | | | | | | | |
| (further coating | | Epoxysilane | | | | | | | | | | | | | |
| additives if present) | | Total (Constituent 3) | | | | | | | | | | | | | |

| | | Composition # | 14 | 15 | 16 | 17 | 18 | 19 | 20 | 21 |
|---|---|---|---|---|---|---|---|---|---|---|
| Constituent 1 | | 15579-50630 | | | 108.4 | 108.4 | | | | |
| (Epoxy resin | | BPA-Epoxy 1 | 30.0 | 30.0 | | | 30.0 | 30.0 | | |
| compositions) | | Butanol | 5.0 | 5.0 | | | 5.0 | 5.0 | 2.5 | 2.5 |
| | | Xylene | | | | | | | 12.5 | 12.5 |
| | | Adhesion promoter | 3.0 | 3.0 | 3.1 | 3.1 | 3.0 | 3.0 | | |
| | | BPA-Epoxy 2 | | | | | | | 10.6 | 10.6 |
| | | Vinyl resin | | | | | | | 10.0 | 10.0 |
| | | Total (Constituent 1) | 38.0 | 38.0 | 111.5 | 111.5 | 38.0 | 38.0 | 35.6 | 35.6 |
| Constit-<br>uent 2 | Step 1 | Epoxysilane | | | | | | | | |
| | | Vinyltrimethoxysilane | | | | 1.5 | | | | |
| (Curing | | Mannich base 1 | 11.2 | 11.2 | | | | | 11.2 | 11.2 |
| Agent) | | 1,3-BAC | | | | | | | | |
| | | Methanol | | | | | | | | |
| | | Xylene | 7.2 | 7.2 | 7.2 | 7.2 | 7.2 | 7.2 | 7.2 | 7.2 |
| | | Mannich base 2 | | | | | | | | |
| | | Mannich base 3 | | | | | | | | |
| | | Polyaminoamide | | | 6.5 | | 6.5 | 6.5 | | |
| | | Novolac epoxy | | | | | | | | |
| | | BPA-Epoxy 2 | 0.8 | 0.8 | | | 0.8 | 0.8 | 0.8 | 0.8 |
| | Step 2 | Epoxysilane | | | | | | | 3.4 | |
| | | Vinyltrimethoxysilane | | | | | | | 1.5 | |
| | | Mannich base 3 | | | | | | | | |
| | | Total (Constituent 2) | 19.2 | 19.2 | 15.2 | 13.7 | 14.5 | 74.5 | 24.1 | 79.2 |
| Constituent 3 | | Aminosilane | | 3.5 | | | | 3.5 | | |
| (further coating | | Epoxysilane | 3.5 | | 3.5 | 3.5 | 3.5 | | | 3.5 |
| additives if present) | | Total (Constituent 3) | 3.5 | 3.5 | 3.5 | 3.5 | 3.5 | 3.5 | | 3.5 |

All entries in the table above are in wet weight (gram)

TABLE 3a

Tiecoat compositions

| | | Composition # | 22 | 23 | 24 | 25 | 26 | 27 | 28 | 29 |
|---|---|---|---|---|---|---|---|---|---|---|
| Component 1 | | Rutile titanium dioxide | 2.6 | 2.6 | 2.6 | 2.6 | 2.6 | 2.6 | 2.6 | 2.6 |
| (Epoxy resin | | Black iron oxide | 1.1 | 1.1 | 1.1 | 1.1 | 1.1 | 1.1 | 1.1 | 1.1 |
| compositions) | | Rheological agent | 0.4 | 0.4 | 0.4 | 0.4 | 0.4 | 0.4 | 0.4 | 0.4 |
| | | Extender pigment | 15.0 | 15.0 | 15.0 | 15.0 | 15.0 | 15.0 | 15.0 | 15.0 |
| | | BPA-Epoxy 1 | | | | | | | | |
| | | Butanol | 2.5 | 2.5 | 2.5 | 2.5 | 2.5 | 2.5 | 2.5 | 2.5 |
| | | Xylene | 25.0 | 25.0 | 25.0 | 25.0 | 25.0 | 25.0 | 25.0 | 25.0 |
| | | Adhesion promoter | 1.5 | 3.0 | | | 3.0 | 3.0 | 3.0 | 3.0 |
| | | BPA-Epoxy 2 | 10.6 | 10.6 | 10.6 | 10.6 | 10.6 | 10.6 | 10.6 | 10.6 |
| | | Vinyl resin | 10.0 | 10.0 | 10.0 | 10.0 | 10.0 | 10.0 | 10.0 | 10.0 |
| | | Total (component 1) | 68.7 | 70.2 | 67.2 | 67.2 | 70.2 | 70.2 | 70.2 | 70.2 |
| Compo-<br>nent 2 | Step 1 | Epoxysilane | | | | | | | 3.4 | |
| | | Vinyltrimethoxysilane | | | | | | | 1.5 | 1.5 |
| (Curing | | Mannich base 1 | 11.2 | 11.2 | 11.2 | 11.2 | 2.4 | 11.2 | 11.2 | 11.2 |
| Agent) | | 2-(3,4 epoxycyclohexyl) | | | | | | | | 3.6 |
| | | (m-XDA) styrene adduct | | | | | 5.9 | | | |

TABLE 3a-continued

| | Tiecoat compositions | | | | | | | | |
|---|---|---|---|---|---|---|---|---|---|
| | Composition # | 22 | 23 | 24 | 25 | 26 | 27 | 28 | 29 |
| Step 2 | Xylene | 7.2 | 7.2 | 7.2 | 7.2 | 7.2 | 7.2 | 7.2 | 7.2 |
| | BPA-Epoxy 2 | 0.8 | 0.8 | 0.8 | 0.8 | 0.8 | 0.8 | 0.8 | 0.8 |
| | Epoxysilane | 3.4 | 3.4 | 3.4 | | 3.4 | | | |
| | Vinyltrimethoxysilane | 1.5 | 1.5 | 1.5 | | 1.5 | | | |
| | Total (component 2) | 24.1 | 24.1 | 24.1 | 19.2 | 21.2 | 19.2 | 24.1 | 24.3 |
| Component 3 (further coating additives if present) | Aminosilane | | | | | | 3.5 | | |
| | VOS-capped PDMS | | | 4.2 | 4.2 | | | | |
| | Epoxysilane | | | | | | | | |
| | Total (component 3) | | | 4.2 | 4.2 | | 3.5 | | |

All entries in the table above are in wet weight (gram)

Description of Tiecoat Compositions—Table 3
Compositions 1-3
Compositions 1-3 contain a high molecular weight aminosilane adduct according to the invention which is the reaction product of Mannich base 1-3 with epoxysilane and a substoichiometric amount of liquid epoxy (BPA-Epoxy 2). The curing agent contains an alkoxysilane of the formula $Si(R^b)_v(OR^c)_{4-v}$ (in this example vinyltrimethoxysilane is used). The compositions further comprise a silanol terminated polydimethylsiloxane adhesion promoter and a solid epoxy (BPA-Epoxy 1).
Compositions 4-5
Compositions 4-5 contain a high molecular weight aminosilane adduct according to the invention which is the reaction product of a polyaminoamide with epoxysilane and a substoichiometric amount of liquid epoxy (BPA-Epoxy 2). The curing agent contains an alkoxysilane of the formula $Si(R^b)_v(OR^c)_{4-v}$ (in these examples vinyltrimethoxysilane is used). The compositions further comprise a silanol terminated polydimethylsiloxane adhesion promoter and a solid epoxy (BPA-Epoxy 1). Composition 5 comprises fillers, pigments and thixotropy elements in Constituent 1 (a formulated, commercial anticorrosive primer base, 15579-50630)
Composition 6
Composition 6 contains a high molecular weight aminosilane adduct according to the invention which is the reaction product of 1,3-Cyclohexanebis(methylamine) (1,3-BAC) with a substoichiometric amount of liquid epoxy (BPA-Epoxy 2), novolac epoxy (novolac epoxy) and an epoxysilane. The curing agent contains an alkoxysilane of the formula $Si(R^b)_v(OR^c)_{4-v}$ (in this example vinyltrimethoxysilane is used). The compositions further comprise a silanol terminated polydimethylsiloxane adhesion promoter and a solid epoxy (BPA-Epoxy 1).
Composition 7
Composition 7 contains a high molecular weight aminosilane adduct according to the invention which is the reaction product of Mannich base 1 with epoxysilane and a substoichiometric amount of liquid epoxy (BPA-Epoxy 2). The aminosilane adduct further contains a mannich base (Mannich base 3) which is not a part of the aminosilane adduct. The curing agent further comprise an alkoxysilane of the formula $Si(R^b)_v(OR^c)_{4-v}$ (in this example vinyltrimethoxysilane is used), a silanol terminated polydimethylsiloxane adhesion promoter and a solid epoxy (BPA-Epoxy 1).
Compositions 8 and 10:
Compositions 8 and 10 contain a high molecular weight aminosilane adduct according to the invention which is the reaction product of Mannich base 1 and 3 (composition 8 corresponds to Mannich base 3 and composition 10 corresponds to Mannich base 1) with epoxysilane and a substoichiometric amount of liquid epoxy (BPA-Epoxy 2). The curing agent contains an alkoxysilane of the formula $Si(R^b)_v(OR^c)_{4-v}$ (in this example vinyltrimethoxysilane is used). The compositions further comprise a silanol terminated polydimethylsiloxane adhesion promoter and a liquid epoxy (BPA-Epoxy 2).
Compositions 9 and 11:
Composition 9 corresponds to composition 8, but further comprising a vinyl resin. Composition 11 corresponds to composition 10, but further comprising a vinyl resin.
Composition 12:
Composition 12 contains a high molecular weight aminosilane adduct according to the invention which is the reaction product of Mannich base 1-3 with epoxysilane. The curing agent contains an alkoxysilane of the formula $Si(R^b)_v(OR^c)_{4-v}$ (in this example vinyltrimethoxysilane is used). The compositions further comprise a silanol terminated polydimethylsiloxane adhesion promoter, a liquid epoxy (BPA-Epoxy 2) and a vinyl resin.
Composition 13:
Composition 13 corresponds to composition 11, but the alkoxysilane has been replaced with methanol.
Reference Compositions 14-19:
Ref. Composition 14:
Composition 14 contains only an epoxysilane, which is added to the composition just before application. Therefore, this composition does not comprise a high molecular weight aminosilane adduct. The binder system comprise a high molecular weight Mannich base adduct, which is the reaction product of Mannich base 1 with a substoichiometric amount of liquid epoxy (BPA-Epoxy 2). The compositions further comprise a silanol terminated polydimethylsiloxane adhesion promoter and a solid epoxy (BPA-Epoxy 1).
Ref. Composition 15:
Ref. Composition 15 is identical to composition 14, but the epoxysilane has been replaced by aminosilane 1:1 by weight (Mw=222 g/mol), which is added to the composition just before application. Therefore, these compositions does not comprise a high molecular weight aminosilane adduct.
Ref. Composition 16-17:
Ref. Composition 16-17 contains only an epoxysilane, which is added to the composition just before application. Therefore, these compositions does not comprise a high molecular weight aminosilane adduct. The binder system comprise a high molecular weight polyaminoamide adduct, which is the reaction product of polyaminoamide with a substoichiometric amount of liquid epoxy (BPA-Epoxy 2).

Composition 16 further comprise an alkoxysilane of the formula $Si(R^b)_v(OR^c)_{4-v}$ (in this example vinyltrimethoxysilane is used). Both compositions comprise a silanol terminated polydimethylsiloxane adhesion promoter and a solid epoxy (BPA-Epoxy 1). Both compositions comprise fillers, pigments and thixotropy elements in Constituent 1 (a formulated, commercial anticorrosive primer base, 15579-50630).

Ref. Composition 18:

Ref. Composition 18 contains only an epoxy silane, which is added to the composition just before application. Therefore, this composition does not comprise a high molecular weight aminosilane adduct. The binder system comprise a high molecular weight polyaminoamide adduct, which is the reaction product of polyaminoamide with a substoichiometric amount of liquid epoxy (BPA-Epoxy 2). The compositions further comprise a silanol terminated polydimethylsiloxane adhesion promoter and a solid epoxy (BPA-Epoxy 1).

Ref. Composition 19:

Composition 19 is identical to composition 18, but the epoxysilane has been replaced by aminosilane 1:1 by weight (Mw=222 g/mol), which is added to the composition just before application. Therefore, this composition does not comprise a high molecular weight aminosilane adduct.

Composition 20:

Composition 20 comprises a high molecular weight aminosilane adduct according to the invention which is the reaction product of Mannich base 1 with epoxysilane and a substoichiometric amount of liquid epoxy (BPA-Epoxy 2). The curing agent contains an alkoxysilane of the formula $Si(R^b)_v(OR^c)_{4-v}$ (in this example vinyltrimethoxysilane is used). The composition further comprises a solid epoxy (BPA-Epoxy 1). The composition is devoid of polysiloxane adhesion promoter.

Ref. Composition 21:

Composition 21 contains only an epoxy silane, which is added to the composition just before application. Therefore, this composition does not comprise a high molecular weight aminosilane adduct. The composition comprises a curing agent which is the reaction product of Mannich base 1 with a substoichiometric amount of liquid epoxy (BPA-Epoxy 2). The curing agent contains an alkoxysilane of the formula $Si(R^b)_v(OR^c)_{4-v}$ (in this example vinyltrimethoxysilane is used). The composition further comprises a solid epoxy (BPA-Epoxy 1). The composition is devoid of polysiloxane adhesion promoter.

Composition 22:

Composition 22 contain a high molecular weight aminosilane adduct according to the invention which is the reaction product of Mannich base 3 with epoxysilane and a substoichiometric amount of liquid epoxy (BPA-Epoxy 2). The curing agent contains an alkoxysilane of the formula $Si(R^b)_v(OR^c)_{4-v}$ (in this example vinyltrimethoxysilane is used). The compositions further comprise a silanol terminated polydimethylsiloxane adhesion promoter and a liquid epoxy (BPA-Epoxy 2). The composition is comparable to composition 10, but further comprises fillers and pigments to form a model paint composition.

Composition 23:

Composition 23 corresponds to Composition 22, but contains twice the amount of adhesion promoter used in composition 22.

Composition 24:

Composition 24 corresponds to Composition 23, but the silanol terminated adhesion promoter has been replaced with a VOS-capped polydimethyl siloxane according to the invention.

Reference Composition 25:

Reference Composition 25 corresponds to Composition 24, but does not contain a high molecular weight aminosilane.

Composition 26:

Composition 26 corresponds to Composition 23, but further comprise another amine (m-XDA styrene adduct) as raw material for the synthesis of the high molecular weight aminosilane according to the invention.

Reference Composition 27:

Reference Composition 27 corresponds to Composition 23, but contains a low-molecular weight aminosilane in replacement for the high molecular weight aminosilane.

Composition 28:

Composition 28 consist of the same raw materials as composition 23, but the curing agent has been produced in a one-step reaction according to the invention.

Composition 29:

Composition 29 is prepared in a one-step reaction and is comparable to composition 28, but the epoxy silane used for the synthesis of the high molecular weight aminosilane has been replaced with 2-(3,4 epoxycyclohexyl) ethyltrimethoxysilane according to the invention.

Preparation of Test Panels

Glass Substrate

Glass panels size 100×150 mm were machine washed and dried before use. The glass panels were used as an inert, non-porous substrate.

Substrate with Anticorrosive Surface

Cold rolled, sandblasted steel panels (70×150×3 mm) were coated with 75-100μ (dry film thickness, DFT) of commercial anticorrosive epoxy primer (Hempadur 15570-50630, Hempel A/S) using airless spray. After 24 h of drying at room temperature, 20° C., 40% relative humidity (RH), the panels were recoated with the experimental tiecoat(s) using a doctor blade with 300μ clearance. The tiecoat layer is cured under various conditions (temperature, relative humidity) according to experimental setup shown in the tables below) before application of topcoat. The topcoat (Hempasil X3 87500 or Intersleek® 970 or Intersleek® 757 according to specification) is applied using a doctor blade so that it forms a dry film thickness (DFT) of 170μ when dried and cured. The curing interval before performing the adhesion test is specified in the individual examples.

Substrate with Antifouling Surface

Acrylic panels (150×200×5 mm), sandblasted on one side to facilitate adhesion of the coating, are coated with 100 μm (DFT) of a commercial epoxy (HEMPEL's Light Primer 45551) applied by air spraying. After 6 h of drying at room temperature an antifouling coat of the type HEMPEL'S ANTIFOULING GLOBIC NCT 8190N ex. Hempel A/S is applied by doctor blade with 400 μm clearance. The panels are dried for at least 72 h before immersion into sea water with salinity in the range of 37-38 parts per thousand at an average temperature of 17-18° C. The antifouling coated panels are permanently immersed in static conditions for a period of 72 weeks. After exposure, the panels are cleaned using high pressure freshwater wash to remove any fouling and subsequently dried for 1 week at room temperature (20° C., 40% RH). The panels were recoated with the experimental tiecoat(s) using a doctor blade with 150μ clearance. The tiecoat layer is cured for 8 h at 20° C., 40% RH before application of topcoat. The topcoat (Hempasil X3 87500) is applied in a dry film thickness (DFT) of 170μ using a doctor blade and cured for 24 h at the same curing conditions as the tiecoat before adhesion testing.

Panels for Immersion Test

In a spraying cabin with climate control, mild steel panels (150×75×3 mm) blasted to minimum Sa 2½ (ISO 8501-1) with a surface profile equivalent to Fine (G) (ISO 8503-1) are coated with 150 μm (dry film thickness, DFT) of a commercial epoxy primer (HEMPADUR Quattro 17634) using airless spraying equipment. The curing conditions (temperature and humidity) are kept constant throughout the application and curing steps until final exposure. After 24 hours of curing, the tiecoat compositions are applied by doctor blade of 300 μm clearance, with an internal width of 60 mm, and allowed to cure for a further specified time. In the instance that an intermediate tiecoat is applied, it is applied using doctor blade of 500μ clearance with an internal width of 60 mm and allowed to cure for a further specified time. After drying, the top coat paint compositions are applied by doctor blade of 400 μm clearance with an internal width of 50 mm. The panels are cured for 24 hours before exposure in the Immersion test.

Test Methods

Molecular Weight Determination

Molecular sizes were measured using gel permeation chromatography (1260 series from Agilent technology). The columns were 2 PL Gel 5 μm mixed C followed by 1 PL Gel 5 μm 50Å(ex. Polymer Labs) all 3 connected serially. As detector, an Evaporative Light Scattering Detector (380 ELSD ex. Agilent technologies) was used. The ELSD detector was operated with a nebulizer temperature at 40° C., an evaporation temperature at 35° C. and with a nitrogen gas flow at 1.2 SLM (Standard Litre per. Minute). The measurements were performed at a column temperature at 25.0 degrees celsius and at a flow rate of 1.0 ml/min of filtered tetrahydrofuran (technical grade containing 250 ppm tertiary butyl hydroxy toluene as inhibitor) with added 5% methanol and 0.5% triethylamine (both technical grades) as eluent. The injected volume was 50 μl of a concentration of approximately 0.02 g of the adducts in THF (technical grade).

Molecular weights were determined as the weight average molecular weights using ChemStation GPC Data Analysis Software (rev. B.01.01) available from Agilent technologies. Peaks corresponding to unreacted starting material were not included in the analysis. For the calibration, seven narrow polystyrene standards were used. The standards weigh 1,200,000 (ex. Waters); 128,000 (ex. Polymer labs); 39,000 (ex. Polymer labs); 5,700 (ex. Polymer labs); 950 (ex. Polymer labs); 278 (ex. Polymer labs); 92 (ex. Polymer labs) Da respectively. The calibration curve was fitted to a 3rd degree polynomial regression.

Adhesion Test

The adhesion of a coating formulation to a surface is tested by a crosscut peel test according to the following procedure. Using a knife, two perpendicular cuts are made in a cross (X) shape. By rubbing from the centre of the cross and outwards using a finger, removal of the polysiloxane coating is attempted.

The coating is considered to pass the test if there is only a cohesive failure in the layer to be tested and no adhesive failure between the layer and the surface.

The coating is considered to fail if there is an adhesive failure between any layer and another layer or between the layer and the surface.

Immersion Test

The Immersion test outlined herein may be used to determine the resistance to water exposure, in particular adhesion and blistering.

The water used is tap water and the temperature of the water is kept constant at 22° C.

Panels are exposed for two weeks and checked after one week of exposure and after two weeks of exposure.

Adhesion of the various paint layers is evaluated according to adhesion test described in previous section "Adhesion test". Blistering tendency is evaluated according to ASTM D 714.

Results

Example 1

Effect of pre-reacting the epoxy silane to the high molecular weight amine. Influence on topcoat adhesion at a temperature range. Adhesion evaluated after 24 h. Glass substrates were used.

| Curing conditions | RC-int. (h) | Composition # | Adhesion of 87500-59151 |
|---|---|---|---|
| 20° C., 40% RH | 8 | 1 | Pass |
|  |  | 11 | Pass |
|  |  | 13 | Pass |
|  |  | 14 (reference) | Pass |
|  |  | 15 (reference) | Pass |
| 10° C., 75% RH | 8 | 1 | Pass |
|  |  | 11 | Pass |
|  |  | 13 | Pass |
|  |  | 14 (reference) | Fail |
|  |  | 15 (reference) | Fail |
| 0° C., 65% RH | 24 | 1 | Pass |
|  |  | 11 | Pass |
|  |  | 13 | Pass |
|  |  | 14 (reference) | Fail |
|  |  | 15 (reference) | Fail |

Compositions 1, 11 and 13 all comprise high molecular weight aminosilane adducts, where compositions 11 and 13 differs by comprising/not comprising an alkoxysilane, respectively. Composition 14 and 15 are reference examples, where the organosilane has not been pre-reacted with a high molecular weight amine. The high molecular weight amine (based on Mannich base 1) is used to prepare the high molecular weight aminosilane adduct in composition 1, 11 and 13 is also used as curing agent in reference compositions 14 and 15. It demonstrates that, at temperatures below 20° C., the compositions with pre-reacted silanes are the only compositions that pass the adhesion test. The example also demonstrates that the water scavenger, an alkoxysilane, is not necessary for providing topcoat adhesion, by comparing composition 11 with composition 13.

Example 2

Examples of alternative high molecular weight aminosilane adducts. Fouling release topcoat adhesion at 20° C. Adhesion evaluated after 24 h. Glass substrates were used.

| Curing conditions | RC-int. (h) | Composition # | Adhesion of 87500-59151 |
|---|---|---|---|
| 20° C., 40% RH | 8 | 1 | Pass |
| | | 2 | Pass |
| | | 3 | Pass |
| | | 4 | Pass |
| | | 6 | Pass |
| | | 12 | Pass |

Example 2 demonstrates variations of high molecular weight amines to prepare the high molecular weight aminosilane adduct according to the invention. Composition 1-3: Mannich bases which have been pre-reacted with a substoichiometric liquid BPA-Epoxy (BPA-Epoxy 2) and further reacted with epoxysilane to form a high molecular weight aminosilane; Composition 4: A polyaminoamide which has been pre-reacted with a substoichiometric liquid BPA-Epoxy (BPA-Epoxy 2) and further reacted with epoxysilane to form a high molecular weight aminosilane adduct; Composition 6: A primary amine (1,3-BAC), which has been pre-reacted with a substoichiometric liquid BPA-Epoxy (BPA-Epoxy 2) and a novolac epoxy (Novolac epoxy) and further reacted with epoxysilane to form a high molecular weight aminosilane adduct; Composition 12: Mannich base 1 which has been reacted with a epoxysilane to form a high molecular weight aminosilane adduct). All compositions pass the adhesion test.

Example 3

Examples of alternative epoxy-based binder systems used with curing agents comprising a Mannich base. Adhesion evaluated after 24 h. Glass substrates were used.

| Curing conditions | RC-int. (h) | Composition # | Adhesion of 87500-59151 |
|---|---|---|---|
| 10° C., 70% RH | 8 | 1 | Pass |
| | | 7 | Pass |
| | | 8 | Pass |
| | | 9 | Pass |
| | | 10 | Pass |
| | | 11 | Pass |
| | | 12 | Pass |
| | | 14 (reference) | Fail |
| | | 15 (reference) | Fail |

Compositions 1, 7, 8, 9, 10, 11, 12 all comprised a liquid epoxy (BPA-Epoxy 2) binder cured with a high molecular weight aminosilane adduct comprising a Mannich base. Compositions 9, 11 and 12 further comprise a vinyl resin. Reference examples 14 and 15 are solid epoxy (BPA-Epoxy 1) cured with a high molecular weight amine adduct comprising a Mannich base (Mannich base 1) and a substoichiometric amount of liquid epoxy (BPA-Epoxy 2). They further comprise epoxysilane and aminosilane, respectively, which were added before application. It is demonstrated that the binder system does not need to comprise a solid epoxy. It is also demonstrated that a vinyl resin can be used as binder extender. It is further demonstrated that the silane needs to be of high molecular weight to provide topcoat adhesion at temperatures below 20° C.

Example 4

Polyaminoamide Binder Matrix

| Curing conditions | RC-int. (h) | Composition # | Adhesion of 87500-59151 |
|---|---|---|---|
| 10° C., 70% RH | 8 | 4 | Pass |
| | | 18 (reference) | Fail |
| | | 19 (reference) | Fail |

The example constitutes an alternative binder matrix. In this example the curing agent comprises a polyaminoamide high molecular weight amine. In composition 4, the high molecular weight polyaminoamide has been further reacted with an epoxysilane to form a high molecular weight aminosilane adduct according to the invention. Reference examples 18 and 19 comprise a polyaminoamide and epoxy- and aminosilane, respectively, which have not been pre reacted to the high molecular weight polyaminoamide adduct. The example demonstrates, that the use of an alternative curing agent provides topcoat adhesion below 20° C., and reference examples 18 and 19 demonstrates that silanes which have not been reacted to a high molecular weight binder fails to provide topcoat adhesion below 20° C., when utilizing a high molecular weight polyaminoamide adduct as curing agent.

Example 5

Effect of porous substrates on fouling release topcoat adhesion at 20° C. Adhesion evaluated after 24 h. Two types of substrate were compared: glass substrates and substrates with an aged antifouling surface (aged 8190N, ex. Hempel A/S).

| Substrate | RC-int. (h) | Composition # | Adhesion of 87500-59151 |
|---|---|---|---|
| Glass | 8 | 5 | Pass |
| | | 16 (reference) | Pass |
| | | 17 (reference) | Pass |
| 8190N, aged antifouling surface | | 5 | Pass |
| | | 16 (reference) | Fail |
| | | 17 (reference) | Fail |

All compositions comprise a formulated epoxy primer base composition (Hempadur 15579-50630 ex. Hempel, constituting a solid epoxy, fillers, pigments, solvents, plasticizers, thixotropic agents). Composition 5 is cured with an high molecular weight aminosilane adduct made from a high molecular weight polyaminoamide adduct which has been reacted with an epoxysilane and further comprising an alkylalkoxysilane (vinyltrimethoxysilane) according to the invention. Composition 16 is the same epoxy primer base composition as Composition 5, but cured with high molecular weight polyaminoamide adduct and further comprising an alkylalkoxysilane (vinyltrimethoxysilane) and an epoxysilane as a third component. Composition 17 is identical to composition 16, but without the alkylalkoxysilane. Using a non-porous, inert glass substrate all compositions provide adhesion to the topcoat. On the aged antifouling surface, only composition 5 provides topcoat adhesion. The example demonstrates that when using an epoxysilane which is not prereacted to the binder, it does not solve the problem of coating on an antifouling coat. The example also demonstrates that the addition of an alkylalkoxysilane has no effect on the adhesion of the topcoat in the compositions.

Example 6

Adhesion of Various Fouling Release Topcoats

| Tiecoat composition # | Over-coated after | Adhesion evaluated after | Curing conditions | 87500-59151 | IS-970 | IS-757 |
|---|---|---|---|---|---|---|
| 1 | 8 h | 24 h | 20° C., 40% RH | Pass | Pass | Pass |
|   | 24 h |   | 5° C., 75% RH | Pass | Pass | Pass |
|   | 24 h |   | 0° C., 65% RH | Pass | Pass | Pass |

Example 6 shows the adhesion of three different commercial fouling release topcoats to tiecoat Composition 1 according to the invention. Hempasil 87500-59151 (87500-59151) is a silicone hydrogel composition, Intersleek 757 (IS-757) is a silicone elastomer foul release Coating and Intersleek 970 (IS-970) is a fluoropolymer foul release coating. All three topcoats pass the adhesion test in the temperature range and recoating intervals specified in the example.

Example 7

Adhesion of tiecoat compositions to different surfaces at 20° C., 40% RH. Adhesion evaluated after 24 h.

| Substrate | RC-int. (h) | Composition # | Adhesion of tiecoat composition |
|---|---|---|---|
| Glass | n.a. | 1 | Pass |
|   |   | 4 | Pass |
|   |   | 5 | Pass |
|   |   | 10 | Pass |
|   |   | 11 | Pass |
|   |   | 12 | Pass |
| 8190N, aged antifouling surface | n.a. | 5 | Pass |
| 15570-50630, Anticorrosive surface | 24 | 1 | Pass |
|   |   | 4 | Pass |
|   |   | 5 | Pass |
|   |   | 10 | Pass |
|   |   | 11 | Pass |
|   |   | 12 | Pass |

The example constitutes a selection of the binder systems used in the invention. All compositions prove to have good adhesion to the various substrates.

Example 8

Compositions Devoid of Adhesion Promoter

| Tiecoat composition # | Over-coated after | Curing conditions | 87500-59151 (150μ DFT) | 27500-23410 (120μ DFT) + 87500-59151 (150μ DFT) | IS-970 (150μ DFT) | IS-737 (100μ DFT) + IS-970 (150μ DFT) |
|---|---|---|---|---|---|---|
| 20 | 24 h | 20° C., 40% RH | Fail | Pass | Fail | Pass |
|   | 24 h | 10° C., 65% RH | Fail | Pass | Fail | Pass |
|   | 24 h | 0° C., 65% RH | Fail | Pass | Fail | Pass |
| 21 (reference) | 24 h | 20° C., 40% RH | Fail | Pass | Fail | Pass |
|   | 24 h | 10° C., 65% RH | Fail | Pass | Fail | Pass |
|   | 24 h | 0° C., 65% RH | Fail | Fail** | Fail | Fail* |

*Adhesion of IS-737 to composition 21 does not pass the adhesion test
**Adhesion of 27500-23410 to composition 21 does not pass the adhesion test The adhesion was evaluated 24 h after topcoat application.

Example 8 shows a composition comprising a high molecular weight aminosilane adduct according to the invention devoid of adhesion promoter (composition 20) and a reference composition comprising a high molecular weight amine adduct devoid of adhesion promoter (composition 21) at temperature range. The example demonstrates the importance of the adhesion promoter for topcoat adhesion directly to the tiecoat compositions. When the adhesion promoter is left out, the topcoat does not pass the adhesion test on the tiecoat composition. The example further demonstrates that when including an intermediate tiecoat, the adhesion promoter can be omitted and still obtaining good adhesion when using a composition comprising a high molecular weight aminosilane adduct according to the invention, surprisingly even down to 0° C. Comparing the results with reference composition 21 comprising a high molecular weight amine adduct with an epoxy silane added as third component immediately prior to application, it is observed, that at 0° C., the intermediate tiecoat compositions (27500-23410 and IS-737) does not pass the adhesion test. This demonstrates the need for a high molecular weight aminosilane to obtain good adhesion at low temperatures.

Example 9

Exposure of Tiecoat Compositions 14 steels panels were prepared according to procedure described previously in the section "Panels for Immersion test" in the sense that a coat of the tiecoat composition was applied followed by a coat of fouling release topcoat (Hempasil X3; 87500-59151) after a specified time interval. The panels were used for immersion test.

TABLE 4

Overview of test panels for exposure in immersion test

| Test panel # | Tiecoat Composition # | Curing conditions | Overcoat interval (tiecoat composition to topcoat) [hours] |
|---|---|---|---|
| A | 22 | 20° C., 50% RH | 8 |
| B | 1 | 20° C., 50% RH |  |
| C | 23 | 20° C., 50% RH |  |
| D | 24 | 20° C., 50% RH |  |
| E | 25 | 20° C., 50% RH |  |
| F | 26 | 20° C., 50% RH |  |
| G | 11 | 20° C., 50% RH |  |
| H | 12 | 20° C., 50% RH |  |

TABLE 4-continued

Overview of test panels for exposure in immersion test

| Test panel # | Tiecoat Composition # | Curing conditions | Overcoat interval (tiecoat composition to topcoat) [hours] |
|---|---|---|---|
| I | 15 | 20° C., 50% RH | |
| J | 27 | 20° C., 50% RH | |
| K | 29 | 20° C., 50% RH | |
| L | 28 | 5° C., 40% RH | |
| M | | 10° C., 80% RH | |
| N | | 20° C., 50% RH | |

The panels were exposed and inspected according to the description above in section "Immersion test". The results are shown in table 5 below.

Table 5: Results from the Immersion test

| Test panel # | Composition | Tiecoat composition | | 87500-59151 | |
|---|---|---|---|---|---|
| | | 1 week | 2 weeks | 1 week | 2 weeks |
| A | 22 | PASS/10 | PASS/10 | PASS/10 | PASS/10 |
| B | 1 | PASS/10 | PASS/10 | PASS/10 | PASS/10 |
| C | 23 | PASS/10 | PASS/10 | PASS/10 | PASS/10 |
| D | 24 | PASS/10 | PASS/10 | PASS/10 | PASS/10 |
| E | 25 | PASS/10 | PASS/10 | FAIL/10 | FAIL/4D |
| F | 26 | PASS/10 | PASS/10 | PASS/10 | PASS/8F |
| G | 11 | PASS/10 | PASS/10 | PASS/10 | PASS/10 |
| H | 12 | PASS/10 | PASS/10 | PASS/10 | PASS/10 |
| I | 15 | PASS/10 | PASS/10 | FAIL/6D | FAIL/6D |
| J | 27 | PASS/10 | PASS/10 | FAIL/4D | FAIL/4D |
| K | 29 | PASS/10 | PASS/10 | PASS/10 | PASS/10 |
| L | 28 | PASS/10 | PASS/10 | PASS/10 | PASS/10 |
| M | | PASS/10 | PASS/10 | PASS/10 | PASS/10 |
| N | | PASS/10 | PASS/10 | PASS/10 | PASS/10 |

It is found that all tiecoat compositions according to the invention have good adhesion to the substrate and pass the immersion test.

Conclusions to Immersion Test

Panels A, G and C (Composition 22, 11 and 23 compared) The compositions are based on a high molecular weight aminosilane adduct according to the invention, but differ in the concentration of adhesion promoter. It is found that both compositions has good topcoat adhesion and pass the adhesion test. It can be concluded that the two different levels of the adhesion promoter both provide good topcoat adhesion. Composition 11 is the binder system of composition 22, and when the two are compared, the effect of effect of fillers and pigments is evident. The topcoat adhesion of Composition 11 and 22 is comparable during the immersion test, and it can thus be concluded that the effect of fillers and pigments is low.

Panels H and G (Composition 12 and Composition 11 compared): Compositions 11 and 12 both comprise a high molecular weight aminosilane according to the invention, but composition 12 is without a substoichiometric amount of BPA-Epoxy 2. It is observed that the both compositions has good topcoat adhesion and pass the adhesion test.

Panels B and I (Composition 1 and reference Composition 15 compared): Composition 1 is cured with a high molecular weight aminosilane according to the invention. Reference Composition 15 is based on the same epoxy binder system, but with the use of a low molecular amino silane to provide a comparable amount of trimethoxysilyl groups. It is observed that the topcoat adhesion on Composition 1, comprising a high molecular weight aminosilane according to the invention, remains good throughout the immersion test, while the topcoat adhesion on reference example 15, comprising a low molecular weight aminosilane, quickly deteriorates after immersion and grows blisters.

Panels D and E (Composition 24 and reference Composition 25 compared): Composition 24 comprise a VOS tipped polydimethyl siloxane as adhesion promoter and a high molecular weight aminosilane according to the invention. Reference Composition 25 is devoid of the high molecular weight aminosilane. It is observed that the topcoat adhesion on Composition 24, comprising a high molecular weight aminosilane according to the invention, remains good throughout the immersion test, while the topcoat adhesion on reference example 25, devoid of high molecular weight aminosilane, is poor. It is concluded, that incorporating a VOS tipped polydimethyl siloxane as adhesion promoter, does not provide topcoat adhesion unless formulated with a high molecular weight aminosilane according to the invention.

Panels F and K (Compositions 26 and 29): The compositions are formulated with two variants of the high molecular weight aminosilane, according to the invention. It is observed that both compositions has good topcoat adhesion, and pass the adhesion test throughout the immersion test.

Panels N and J (Composition 28 and reference Composition 27 compared): Composition 28 is cured with a high molecular weight aminosilane according to the invention. Reference Composition 27 is based on the same, pigmented epoxy binder system, but with the use of a low molecular amino silane to provide a comparable amount of trimethoxysilyl groups. It is observed that the topcoat adhesion on Composition 28, comprising a high molecular weight aminosilane according to the invention, remains good throughout the immersion test, while the topcoat adhesion on reference example 27, comprising a low molecular weight aminosilane, quickly deteriorates after immersion and grows blisters.

Panels L, M and N (Composition 28): The paint system is applied and cured under various climatic conditions and exposed to the immersion test. Good tiecoat- and topcoat adhesion is observed throughout the immersion test and it is concluded that the tiecoat composition provides good topcoat adhesion in the entire temperature range.

Example 10

Exposure of Tiecoat Compositions Including an Intermediate Tiecoat 3 steels panels were prepared according to procedure described previously in the section "Panels for Immersion test" in the sense that a coat of the tiecoat composition was applied followed by an intermediate tiecoat (Hempasil X-Tend 27500-23410) after a specified time interval followed by a coat of fouling release topcoat (Hempasil X3; 87500-59151) after a specified time interval. The panels were exposed to immersion test.

TABLE 5

Overview of test panels for exposure in immersion test with an intermediate tiecoat between tiecoat and topcoat

| Test panel # | Tiecoat Composition # | Curing conditions | Overcoat interval (tiecoat composition to intermediate tiecoat) [hours] | Overcoat interval (Intermediate tiecoat to topcoat) [hours] |
|---|---|---|---|---|
| O | 28 | 5° C., 40% RH | 8 | 12 |
| P | | 10° C., 80% RH | 8 | 12 |
| Q | | 20° C., 50% RH | 8 | 12 |

Intermediate tiecoat: Hempasil X-Tend; 27500-23410
Topcoat: Hempasil X3; 87500-59151

TABLE 6

Results from the Immersion test of paint systems including an intermediate, condensation curable tiecoat

| Test panel #/ composition | Composition | Tiecoat composition 1 week | 2 weeks | 27500-23410 1 week | 2 weeks | 87500-59151 1 week | 2 weeks |
|---|---|---|---|---|---|---|---|
| O | 28 | PASS/10 | PASS/10 | PASS/10 | PASS/10 | PASS/10 | PASS/10 |
| P | | PASS/10 | PASS/10 | PASS/10 | PASS/10 | PASS/10 | PASS/10 |
| Q | | PASS/10 | PASS/10 | PASS/10 | PASS/10 | PASS/10 | PASS/10 |

Panels O, P and Q (Composition 28): The paint system, including and intermediate, condensation curable tiecoat, is applied and cured under various climatic conditions and exposed to the immersion test. Good tiecoat-, intermediate tiecoat- and topcoat adhesion is observed throughout the immersion test and it is concluded that the tiecoat composition provides good adhesion to the intermediate tiecoat in the entire temperature range.

Although the invention has been described in relation to a number of embodiments and examples, the scope of protection is not limited to these, but is instead defined in the enclosed claims.

The invention claimed is:

1. A method for applying a fouling-release coating system to a surface, said method comprising the steps of: (a) applying a tie-coat composition to the surface, wherein said tie-coat composition comprises:

i) a binder system comprising an epoxy resin;

ii) one or more adhesion-promoting agents selected from the group consisting of hydroxy-functional polysiloxanes and $C_{1-4}$-alkoxy-functional polysiloxanes; and iii) an amino-silane adduct of the formula I:

$$\text{HMWA-}\{N(Y)\text{-Q-X}\text{—}Z\}_p \quad (I)$$

wherein:

HMWA-$\{N(Y)\text{—}\}_p$ is a moiety comprising three or more amino groups, at least some of which are primary or secondary amino groups, wherein each —N(Y)— is a secondary or tertiary amine, wherein Y is selected from hydrogen and $C_{1-4}$-alkyl;

p is 1-20;

-Q- is selected from —C($R^1$)$_2$—C($R^2$)(OH)—, —C(=O)—N($R^3$)—, —C($R^1$)$_2$—C($R^1$)$_2$—C(=O)—O—, —C($R^1$)$_2$—C($R^1$)$_2$—C(=O)—N($R^4$)— and

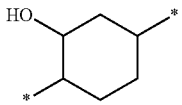

in which each $R^1$ and $R^2$ are independently selected from hydrogen and $C_{1-4}$-alkyl; and $R^3$ and $R^4$ are independently selected from hydrogen, $C_{1-8}$-linear or branched alkyl, vinyl, allyl, aryl and aryl-$C_{1-4}$-alkyl;

—X— is a linker moiety selected from $C_{1-6}$-alkylene which may be optionally substituted with one or more substituents selected from hydroxyl and $C_1$-$C_4$ alkyl; —(CO)—; —NR*—; —O—; —NR*—C(=O)—NR*—; —NR*—C(=O)—; —C(=O)—NR*; -arylene; and combinations thereof, in which R* is selected from H and $C_{1-6}$-alkyl;

—Z is a branched or linear organosiloxane moiety having the molecular formula:

—CH$_2$—[Si($R^a$)$_2$O]$_q$—Si($R^a$)$_3$ in which each $R^a$ is independently selected from $C_{1-8}$-linear or branched alkyl, vinyl, allyl, aryl, aryl-$C_{1-4}$-alkyl, $C_{1-6}$ alkoxy, $C_{3-6}$-alkenyloxy and $C_{3-6}$-alkylideneaminoxyl, with the proviso that at least one $R^a$ is selected from $C_{1-6}$ alkoxy, $C_{3-6}$-alkenyloxy and $C_{3-6}$-alkylideneaminoxyl;

q is an integer from 0-5 inclusive;

wherein the weight average molecular weight of the amino-silane adduct of the formula I is in the range of 500-20000 g/mol;

and (b) subsequently applying a fouling-release top-coat.

2. A method for applying a fouling-release coating system to a surface, said method comprising the steps of: (a) applying a tie-coat composition to the surface, wherein said tie-coat composition comprises:

i) a binder system comprising an epoxy resin;

ii) optionally, one or more adhesion-promoting agents selected from the group consisting of hydroxy-functional polysiloxanes and $C_{1-4}$-alkoxy-functional polysiloxanes; and iii) an amino-silane adduct of the formula I:

$$\text{HMWA-}\{N(Y)\text{-Q-X}\text{—}Z\}_p \quad (I)$$

wherein:

HMWA-$\{N(Y)\text{—}\}_p$ is a moiety comprising three or more amino groups, at least some of which are primary or secondary amino groups, wherein each —N(Y)— is a secondary or tertiary amine, wherein Y is selected from hydrogen and $C_{1-4}$-alkyl;

p is 1-20;

-Q- is selected from —C(R$^1$)$_2$—C(R$^2$)(OH)—, —C(=O)—N(R$^3$)—, —C(R$^1$)$_2$—C(R$^1$)$_2$—C(=O)—O—, —C(R$^1$)$_2$—C(R$^1$)$_2$—C(=O)—N(R$^4$)— and

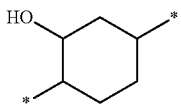

in which each R$^1$ and R$^2$ are independently selected from hydrogen and C$_{1-4}$-alkyl; and R$^3$ and R$^4$ are independently selected from hydrogen, C$_{1-8}$-linear or branched alkyl, vinyl, allyl, aryl and aryl-C$_{1-4}$-alkyl;

—X— is a linker moiety selected from C$_{1-6}$-alkylene which may be optionally substituted with one or more substituents selected from hydroxyl and C$_1$-C$_4$ alkyl; —(CO)—; —NR*—; —O—; —NR*—C(=O)—NR*—; —NR*—C(=O)—; —C(=O)—NR*; -arylene; and combinations thereof, in which R* is selected from H and C$_{1-6}$-alkyl;

—Z is a branched or linear organosiloxane moiety having the molecular formula:

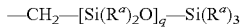

in which each R$^a$ is independently selected from C$_{1-8}$-linear or branched alkyl, vinyl, allyl, aryl, aryl-C$_{1-4}$-alkyl, C$_{1-6}$ alkoxy, C$_{3-6}$-alkenyloxy and C$_{3-6}$-alkylideneaminoxyl, with the proviso that at least one R$^a$ is selected from C$_{1-6}$ alkoxy, C$_{3-6}$-alkenyloxy and C$_{3-6}$-alkylideneaminoxyl;

q is an integer from 0-5 inclusive;

wherein the weight average molecular weight of the amino-silane adduct of the formula I is in the range of 500-20000 g/mol;

(b) applying a condensation-curing tie-coat to the tie-coat of step (a); and (c) subsequently applying a fouling-release top-coat.

3. The method according to claim 1, wherein the HMWA moiety comprises at least one phenolic moiety; and/or wherein the HMWA moiety comprises at least one C$_{7-20}$-aliphatic moiety; and/or wherein the HMWA-{N(Y)—H}$_p$ moiety is the Mannich condensation reaction product of a C$_{7-20}$-alkyl phenol, formaldehyde and one or more amine(s) selected from diamines, triamines or tetraamines, optionally further reacted with a substoichiometric amount of an epoxy-functional resin.

4. The method according to claim 1, wherein the HMWA-{N(Y)—H}$_p$ moiety is the Mannich condensation reaction product of a C$_{7-20}$-alkyl phenol, formaldehyde and one or more amine(s) selected from diamines, triamines or tetraamines, optionally further reacted with a substoichiometric amount of an epoxy-functional resin.

5. The method according to claim 1, wherein q is 1 or 0; and/or wherein p is 1-15; and/or wherein Q is —C(R$^1$)$_2$—C(R$^2$)(OH)—, in which R$^1$ and R$^2$ are both hydrogen; and X is C$_{1-6}$-alkylene.

6. The method according to claim 1, wherein the tie-coat composition additionally comprises one or more alkoxysilanes of the formula (II):

wherein R$^b$ and R$^c$ are independently selected from C$_{1-8}$-linear or branched alkyl, vinyl, allyl, aryl, aryl-C$_{1-4}$-alkyl, C$_{1-6}$ alkoxy, C$_{3-6}$-alkenyloxy and C$_{3-6}$-alkylideneaminoxyl, with the proviso that at least one R$^a$ is selected from C$_{1-6}$ alkoxy, C$_{3-6}$-alkenyloxy and C$_{3-6}$-alkylideneaminoxy, and v is 1, 2 or 3.

7. The method according to claim 1, wherein the tie-coat composition additionally comprises a condensation catalyst.

8. A method for applying a fouling-release coating system to a surface, said method comprising the steps of: (a) applying a tie-coat composition to the surface, wherein said tie-coat composition comprises:
  i) a binder system comprising an epoxy resin;
  ii) one or more adhesion-promoting agents selected from the group consisting of hydroxy-functional polysiloxanes and C$_{1-4}$-alkoxy-functional polysiloxanes; and
  iii) an amino-silane adduct obtained by:
    I. in a first Mannich-type reaction, reacting a C$_{7-20}$-alkyl phenol, formaldehyde and one or more amine(s) selected from diamines, triamines and tetraamines, and optionally further reacting with a substoichiometric amount of an epoxy-functional resin to form a HMWA-{N(Y)—H}$_p$ component in which HMWA-{N(Y)—}$_p$ is a moiety comprising three or more amino groups, at least some of which are primary or secondary amino groups, wherein each —N(Y)— is a secondary or tertiary amine, wherein Y is selected from hydrogen and C$_{1-4}$-alkyl; and p is 1-20; and
    II. in a second reaction, reacting the HMWA-{N(Y)—H}$_p$ component from the first reaction with an epoxy-silane to form an amino-silane adduct;
  wherein the weight average molecular weight of the amino-silane adduct is in the range of 500-20000 g/mol;
and (b) subsequently applying a fouling-release top-coat.

9. A method for applying a fouling-release coating system to a surface, said method comprising the steps of: (a) applying a tie-coat composition to the surface, wherein said tie-coat composition comprises:
  i) a binder system comprising an epoxy resin;
  ii) one or more adhesion-promoting agents selected from the group consisting of hydroxy-functional polysiloxanes and C$_{1-4}$-alkoxy-functional polysiloxanes; and
  iii) an amino-silane adduct obtained by:
    I. in a first reaction, reacting an amino-functional resin with a substoichiometric amount of an epoxy-functional resin or epoxy functional reactive diluent to form a HMWA-{N(Y)—H}$_p$ component, in which HMWA-{N(Y)—}$_p$ is a moiety comprising three or more amino groups at least some of which are primary or secondary amino groups, wherein each —N(Y)— is a secondary or tertiary amine, wherein Y is selected from hydrogen and C$_{1-4}$-alkyl; and p is 1-20,
    II. in a second reaction, reacting the HMWA-{N(Y)—H}$_p$ component from the first reaction with an epoxy-silane to form an amino-silane adduct;
  wherein the weight average molecular weight of the amino-silane adduct is in the range of 500-20000 g/mol;
and (b) subsequently applying a fouling-release top-coat.

10. An article comprising a substrate, said substrate having a surface and a tie-coat on said surface, wherein the tie-coat is prepared from a tie-coat composition as defined in claim 1.

11. An article comprising a substrate, said substrate having a surface and a first tie-coat on said surface, wherein the first tie-coat is prepared from a tie-coat composition as defined in claim 2, said article additionally comprising a condensation-curing tie-coat on said first tie-coat.

12. An article according to claim 10, further comprising a fouling-release coating on said tie-coat(s).

13. A curing agent composition comprising an amino-silane adduct of the formula (Ia) or formula (Ib)

HMWA-{N(Y)—C(R$^1$)$_2$—C(R$^2$)(OH)—X—Z}$_p$     (Ia)

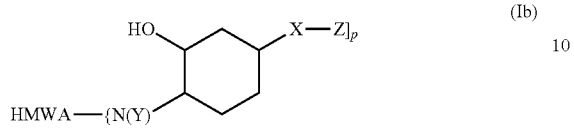
(Ib)

wherein:
HMWA-{N(Y)—}$_p$ is a moiety comprising three or more amino groups, at least some of which are primary or secondary amino groups; wherein each —N(Y)— is a secondary or tertiary amine, wherein Y is selected from hydrogen and C$_{1-4}$-alkyl; wherein said HMWA moiety comprises at least one phenolic moiety and at least one C$_{7-20}$-aliphatic moiety;
each R$^1$ and R$^2$ are independently selected from hydrogen and C$_{1-4}$-alkyl;
p is 1-20;
—X— is a linker moiety selected from C$_{1-6}$-alkylene which may be optionally substituted with one or more substituents selected from C$_1$-C$_4$ alkyl; —O—; and combinations thereof;
—Z is a branched or linear organosiloxane moiety having the molecular formula:

—CH$_2$—[Si(R$^a$)$_2$O]$_q$—Si(R$^a$)$_3$ in which each R$^a$ is independently selected from C$_{1-8}$-linear or branched alkyl, vinyl, allyl, aryl, aryl-C$_{1-4}$-alkyl, C$_{1-6}$ alkoxy, C$_{3-6}$-alkenyloxy and C$_{3-6}$-alkylideneaminoxyl, with the proviso that at least one R$^a$ is selected from C$_{1-6}$ alkoxy, C$_{3-6}$-alkenyloxy and C$_{3-6}$-alkylideneaminoxyl;
q is an integer from 0-5 inclusive;
wherein the weight average molecular weight of the amino-silane adduct is in the range of 500-20000 g/mol.

14. A curing agent composition comprising an amino-silane adduct obtained by:
I. in a first Mannich-type reaction, reacting a C$_{7-20}$-alkyl phenol, formaldehyde and one or more amine(s) selected from diamines, triamines and tetraamines, and optionally further reacting with a substoichiometric amount of an epoxy-functional resin to form a HMWA-{N(Y)—H}$_p$ component in which HMWA-{N(Y)—}$_R$ is a moiety comprising three or more amino groups, at least some of which are primary or secondary amino groups; wherein each —N(Y)— is a secondary or tertiary amine, wherein Y is selected from hydrogen and C$_{1-4}$-alkyl; wherein said HMWA moiety comprises at least one phenolic moiety and at least one C$_{7-20}$-aliphatic moiety; and p is 1-20; and
II. in a second reaction, reacting the HMWA-{N(Y)—H}$_p$ component from the first reaction with an epoxy-silane to form an amino-silane adduct;
wherein the weight average molecular weight of the amino-silane adduct is in the range of 500-20000 g/mol.

15. A tie-coat composition comprising the curing agent composition according to claim 13.

16. The method according to claim 2, wherein the HMWA moiety comprises at least one phenolic moiety; and/or wherein the HMWA moiety comprises at least one C$_{7-20}$-aliphatic moiety; and/or wherein the HMWA-{N(Y)—H}$_p$ moiety is the Mannich condensation reaction product of a C$_{7-20}$-alkyl phenol, formaldehyde and one or more amine(s) selected from diamines, triamines or tetraamines, optionally further reacted with a substoichiometric amount of an epoxy-functional resin.

17. The method according to claim 2, wherein the HMWA-{N(Y)—H}$_p$ moiety is the Mannich condensation reaction product of a C$_{7-20}$-alkyl phenol, formaldehyde and one or more amine(s) selected from diamines, triamines or tetraamines, optionally further reacted with a substoichiometric amount of an epoxy-functional resin.

18. The method according to claim 3, wherein the HMWA-{N(Y)—H}$_p$ moiety is the Mannich condensation reaction product of a C$_{7-20}$-alkyl phenol, formaldehyde and one or more amine(s) selected from diamines, triamines or tetraamines, optionally further reacted with a substoichiometric amount of an epoxy-functional resin.

19. An article according to claim 11, further comprising a fouling-release coating on said tie-coat(s).

20. A tie-coat composition comprising the curing agent composition according to claim 14.

* * * * *